US008278277B2

(12) United States Patent
Uchegbu et al.

(10) Patent No.: US 8,278,277 B2
(45) Date of Patent: Oct. 2, 2012

(54) DELIVERY OF HYDROPHILIC DRUGS

(75) Inventors: Ijeoma Uchegbu, London (GB);
Aikaterini Lalatsa, London (GB);
Andreas Schatzlein, London (GB)

(73) Assignee: University College London, London (GB)

( * ) Notice: Subject to any disclaimer, the term of this patent is extended or adjusted under 35 U.S.C. 154(b) by 494 days.

(21) Appl. No.: 12/420,896

(22) Filed: Apr. 9, 2009

(65) Prior Publication Data

US 2010/0222281 A1 Sep. 2, 2010

(30) Foreign Application Priority Data

Mar. 2, 2009 (GB) .................................. 0903559.3

(51) Int. Cl.
*A61K 38/08* (2006.01)
(52) U.S. Cl. ....... 514/18.5; 514/21.8; 530/302; 530/330
(58) Field of Classification Search .......................... None
See application file for complete search history.

(56) References Cited

U.S. PATENT DOCUMENTS

| 7,741,474 | B2 * | 6/2010 | Uchegbu et al. ............. 536/55.2 |
| 2010/0159014 | A1 * | 6/2010 | Uchegbu et al. ............. 424/489 |

FOREIGN PATENT DOCUMENTS

| FR | 2 735 687 | * | 6/1995 |
| WO | WO 2004/026912 | * | 4/2004 |
| WO | WO 2008/017839 | * | 2/2008 |

OTHER PUBLICATIONS

Prokai-Tatrai et al. "Brain-Targeted Delivery of a Leucine-enkephalin Analogue by Retrometabolic Design," J. Med. Chem., 1996, 39, 4775-4782.*
M. Ahmed et al., "Extraction of Neuropeptides From Joint Tissue for Quantitation by Radioimmunoassay. A study in the Rat", Peptides, 15(2): 317-322 (1994).
K. Barlos et al., "Application of 2-chlorotrityl resin in solid phase synthesis of (Leu15)-gastrin I and unsulfated cholecystokinin octapeptide", Int. J. Peptide Protein Res., 38: 555-561 (1991).
A. Beduneau et al., "Brain targeting using novel lipid nanovectors", Journal of Controlled Release, 126(1): 44-49 (2008).
D. Begley, "The Blood-brain Barrier: Principles for Targeting Peptides and Drugs to the Central Nervous System", J. Pharm. Pharmacol., 48: 136-146 (1996).
D. Begley, "ABC Transporters and the Blood-Brain Barrier", Current Pharmaceutical Design, 10: 1295-1312 (2004).
S. Bihorel et al., "Modulation of the Brain Distribution of Imatinib and its Metabolites in Mice by Valspodar, Zosuquidar and Elacridar", Pharmaceutical Research, 24(9): 1720-1728 (2007).
F. D'Amour et al., "A Method for Determining Loss of Pain Sensation", JPET, 72: 74-49 (1941).

M. L. De Ceballos et al., "Isocratic Reverse-Phase HPLC Separation and RIA Used in the Analysis of Neuropeptides in Brain Tissue", Neuropeptides, 29: 201-209 (1991).
J. Deeken et al., "The Blood-Brain Barrier and Cancer: Transporters, Treatment, and Trojan Horses", Clin. Cancer Res., 13(6): 1663-1674 (2007).
A. Domard et al., "New method for the quaternization of chitosan", Int. J. Biol. Macromol, 8: 105-7 (1986).
J. Girod et al., "Transport of Cationized Anti-Tetanus Fab'2 Fragments Across an In Vitro Blood-Brain Barrier Model: Involvement of the Transcytosis Pathway", Journal of Neurochemistry, 73(5): 2002-2008 (1999).
J. Kreuter et al., "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles", Pharmaceutical Research, 20(3): 409-416 (2003).
W. Lu et al., "Cationic Albumin-Conjugated Pegylated Nanoparticles Allow Gene Delivery into Brain Tumors via Intravenous Administration", Cancer Res., 66(24): 11878-11887 (2006).
J. Mogil et al., "Heritability of nociception I: Responses of 11 inbred mouse strains on 12 measures of nociception", Pain, 80: 67-82 (1999).
W. Pardridge, "The Blood-Brain Barrier: Bottleneck in Brain Drug Development", J. Am. Soc. Exp. NeuroTherap., 2:3-14 (2005).
W. Pardridge, "Drug Targeting to the Brain", Pharmaceutical Research, 24(9): 1733-1744 (2007).
R. Poli et al., "Glycopeptide enkephalin analogues produce analgesia in mice: Evidence for penetration of the blood-brain barrier", Proc. Natl. Acad. Sci. USA, 91: 7114-7118 (1994).
X. Qu et al., "Carbohydrate-Based Micelle Clusters Which Enhance Hydrophobic Drug Bioavailability by Up to 1 Order of Magnitude", Biomacromolecules, 7: 3452-3459 (2006).
N. Shimoyama et al., "d-Methadone is Antinociceptive in the Rat Formalin Test", J. Pharmacol. Exp. Ther., 283(2): 648-52 (1997).
A. Tjolsen et al., "The Tail-flick Latency Is Influenced by Skin Temperature", APS Journal, 2(2): 107-111 (1993).
I. Uchegbu et al., "Quaternary ammonium palmitoyl glycol chitosan—a new polysoap for drug delivery", Int. J. Pharm., 224: 185-199 (2001).
W. Wang et al., "Controls on Polymer Molecular Weight May Be Used to Control the Size of Palmitoyl Glycol Chitosan Polymeric Vesicles", Langmuir, 17: 631-636 (2001).
W. Qinyang et al., "Tissue levels of leu-enkephalin in rats with adjuvant arthritis", J. Neuroimmunol., 158: 34-49 (2005).
I. Uchegbu et al., "Getting Drugs across Biological Barriers—A Role for Nanomedicines", Abstract, INANO Symposium in Innsbruk, Austria on Apr. 10, 2008.
A. Lalatsa et al., "Carbohydrate Nanoparticles for Peptide Delivery to the Central Nervous System", Abstract, 35th Annual CRS Annual Meeting in New York on Jul. 14, 2008.

* cited by examiner

*Primary Examiner* — Christina Bradley
(74) *Attorney, Agent, or Firm* — Saliwanchik, Lloyd & Eisenschenk

(57) ABSTRACT

Compositions comprising a lipophilic derivative of a hydrophilic drug and an amphiphile compound for use in therapy of the human or animal body are provided. Methods of medical treatment, wherein a composition according to the invention is administered to a human or animal body also form part of the invention. It is preferred that the drug is delivered to the brain.

7 Claims, 7 Drawing Sheets

DELIVERY OF HYDROPHILIC DRUGS

FIELD OF THE INVENTION

The present invention relates to a new system for the delivery of hydrophilic drugs to the brain. The system involves forming an endogenously cleavable lipophilic derivative of the hydrophilic drug, and formulating this with an amphiphilic compound. The invention has particular utility for the oral and intra-venous delivery of hydrophilic drugs to the brain.

BACKGROUND TO THE INVENTION

The treatment of diseases of the brain is significantly limited by the blood brain barrier (BBB) (Begley 1996; Begley 2004; Pardridge 2005; Deeken and Loscher 2007), wherein capillaries, characterised by an absence of fenestrae, are surrounded by astrocyte foot processes. Capillary endothelial cells are characterised by tight intercellular junctions, low pinocytotic activity and efflux transporters at their luminal surface. All of these features limit the passage of most molecules into the brain.

Prior brain targeting strategies have involved:

a) exploiting endogenous transporters for carrier mediated uptake (e.g. monoclonal antibody—drug conjugates or monoclonal antibody—particle conjugates) to exploit the human insulin or transferrin receptor (Pardridge 2007; Beduneau et al. 2008);

b) the inhibition of ABC transporters [e.g. P-glycoprotein (Bihorel et al. 2007) and breast cancer resistance protein (Deeken and Loscher 2007)];

c) the use of surfactant coated poly(butylcyanoacrylate) nanoparticles (Kreuter et al. 2003); and d) the use of cationic carriers such as cationic albumin (Lu et al. 2006) and cationised forms of drug molecules (Girod et al. 1999).

All of these strategies use parenteral routes. However, preclinical mouse monoclonal antibody work has not translated into success in the clinic and the inhibition of high capacity ABC transporters, which are not exclusive to the BBB, is also not a viable clinical option.

Most peptide drugs are large in comparison to the vast majority of non-peptide drugs. They typically have molecular weights in excess of 500 Da, which means that diffusion across biological barriers is slow, resulting in poor oral absorption into the blood stream. They are usually hydrophilic and have a significant potential to form hydrogen bonds in aqueous environments. In addition, they often contain several ionisable groups and hence are typically charged at physiological pH. Peptides are also susceptible to degradation within the gastrointestinal tract by carboxy peptidases and amino peptidases. When taken in combination, these factors mean that unmodified peptides are typically very poor candidates for oral delivery, based upon structure alone. Furthermore peptides, even if absorbed are susceptible to degradation within the blood with half lives of a few minutes. Furthermore hydrogen bond formation by hydrophilic peptides limits their transport across the blood brain barrier making neuroactive peptides very difficult to deliver via the oral route.

A wide variety of drug delivery vehicles are known. These include, for instance, liposomes, which are composed of a phospholipid bilayer that may act as a carrier for both hydrophilic and hydrophobic drugs.

WO03/033027 teaches the use of cationic dendrimers (for instance, poly(propylenimine) dendrimers with a diaminobutane core) to deliver bioactive molecules such as polynucleotides or polypeptides to a human or animal recipient.

WO2004/026912 describes solubilising polysaccharides which are used to solubilise hydrophobic drugs. The polysaccharides are amphiphilic and are generally selected from any derivatives of the following: chitosans, dextrans, alginic acids, starches, dextran and guar gums. Quaternary ammonium palmitoyl glycol chitosan (GCPQ) and quaternary ammonium cetyl glycol chitosan (GCHQ) are used in the Examples of this patent application as solubilising polysaccharides.

WO2008/017839 describes micellar clusters formed from amphiphilic carbohydrate polymers and their use in formulating hydrophobic drugs. Palmitoyl glycol chitosan is a specifically exemplified amphiphilic carbohydrate polymer. The Patent Application focuses on improved drug delivery to the CNS or cornea. Gastrointestinal delivery of the drugs is briefly mentioned.

Improved oral delivery of poorly soluble drugs is described in WO2004/026941. Amphiphilic polymers, such as poly (ethylenimine) polymers are used.

At a meeting in Innsbruk Austria on 10 Apr. 2008—the INANO Symposium and at a meeting in New York—the 35$^{th}$ Annual CRS Annual Meeting on 14 Jul. 2008 (Lalatsa A, Schatzlein A G, Uchegbu I F, Carbohydrate nanoparticles for peptide delivery to the central nervous system, Abstract 3279), a method of enhancing the bioavailability of Leucine[5]-Enkephalin was disclosed. Leucine[5]-Enkephalin, a hydrophilic peptide was modified by making it more lipophilic. More specifically, a lipid ester pro-drug of Leucine[5]-Enkephalin was formed and added to a composition comprising quaternary ammonium palmitoyl glycol chitosan (GCPQ). The composition was delivered intravenously. The prodrug was converted to Leucine[5]-Enkephalin in vivo. The lipid ester prodrug with GCPQ was shown to result in significantly higher Leucine[5]-Enkephalin brain levels than when Leucine[5]-Enkephalin alone or Leucine[5]-Enkephalin with GCPQ after I.V. administration were used.

Oral delivery of the lipid ester prodrug was not disclosed at this meeting. Indeed, one would not have expected such a composition to be successfully delivered by the oral route, since peptides are notoriously difficult to administer to the body via this route and the lipidised drug, the amphiphilic prodrug, had a molecular weight in excess of 500 Da.

The prior art does not describe how one can successfully deliver hydrophilic drugs to the brain. This invention addresses this short-coming.

SUMMARY OF THE INVENTION

In accordance with a first aspect of the invention there is provided a composition comprising a lipophilic derivative of a hydrophilic drug and an amphiphile compound for use in therapy of the human or animal body.

In accordance with a second aspect of the invention there is provided a pharmaceutical composition comprising a lipophilic derivative of a hydrophilic drug, an amphiphile compound, and one or more pharmaceutically acceptable excipients.

In accordance with a third aspect of the invention there is provided a method of medical treatment wherein a composition according to the first or second aspect of the invention is administered to a human or animal body.

DETAILED DESCRIPTION OF THE INVENTION

By lipophilic, is meant a compound having very low solubility in water (<0.1 mg/mL). By hydrophilic, is meant a compound with high water solubility (>1 mg/mL).

The invention has particular utility for the delivery of hydrophilic drugs to the brain. We have shown that the drug, delivered in accordance with the invention, is able to cross the blood brain barrier and have a therapeutic effect in the brain.

The lipophilic derivative of the hydrophilic drug typically comprises a hydrophilic drug and a cleavable linker. The derivative may act as a pro-drug which is cleaved to the active drug in the human or animal body, preferably at the drug's target location.

Preferably, the linker is enzymatically cleavable. However, local environmental conditions within the body may alternatively promote cleavage. Low pH, in the range 1-5, and hypoxic conditions are known to promote pro-drug cleavage.

The linker is hydrophobic and renders the hydrophilic drug lipophilic. Typically, the linker comprises a substituted or unsubstituted hydrocarbon group comprising at least 4 carbon atoms, preferably at least 10 or 15 carbon atoms, and comprises, for instance a $C_{4-30}$ alkyl group, $C_{4-30}$ acyl group, a $C_{4-30}$ alkenyl group, a $C_{4-30}$ alkynyl group, a $C_{5-20}$ aryl group, a multicyclic hydrophobic group with more than one $C_4$-$C_8$ ring structure such as a sterol (e.g. cholesterol), a multicyclic hydrophobic group with more than one $C_4$-$C_8$ heteroatom ring structure, a polyoxa $C_1$-$C_4$ alkylene group such as polyoxa butylene polymer, or a hydrophobic polymeric substituent such as a poly(lactic acid) group, a poly(lactide-co-glycolide) group or a poly(glycolic acid) group. The linker may be linear, branched or have cyclo groups.

Preferably, the linker is covalently attached to the hydrophilic drug. However, it need not be, and electrostatic means of association with the hydrophilic drug are also included within the scope of this invention.

Typically, the linker is attached to the hydrophilic drug by means of an acyl group. For instance, the linker may be attached via an ester or an amide linkage, with the nitrogen or oxygen atom of this linkage derived from the hydrophilic drug. For instance, the hydrophilic drug may have an amine or a hydroxyl group which is derivatised by the linker. When the hydrophilic drug is a peptide, such groups may form part of the peptide backbone or of an amino acid's side chain. For instance, the side chain hydroxyl of a tyrosine residue may be derivatised. A particularly preferred linker has the general formula —C(=O)R$^1$, wherein R$^1$ is any of the linkers outlined above and is preferably $C_{4-20}$ alkyl which may be optionally substituted with groups well known in the art, which do not detract from the linker's hydrophobicity.

A particularly preferred linker is derived from palmitic acid, i.e. a palmitoyl group. Other preferred linkers are derived from caprylic, capric, lauric, myristic, stearic and arachidic acids and cholesterol.

The hydrophilic drug is preferably a peptide. Peptides are of tremendous clinical value for the treatment of many central nervous system (CNS) disorders, and preferably therefore the drug is a CNS active drug. Many existing peptide pharmaceuticals are rendered ineffective after oral administration or are unable to cross the blood brain barrier (BBB) on parenteral administration mainly due to their hydrophilicity, size, charge and rapid metabolic degradation in the gastrointestinal tract and blood, as detailed above. Since the invention has particular utility for delivering drugs to the brain, the hydrophilic drug is preferably a neuroactive agent.

Endogenous opioid neuropeptides, preferably neuropentapeptides are particularly preferred drugs for use in this invention. Examples include Met[5]-Enkephalin and Leu[5]-Enkephalin.

The drug may be used to treat brain disorders such as schizophrenia, obesity, pain and sleep disorders, psychiatric diseases, neurodegenerative conditions, brain cancers and infective diseases.

Preferred drugs include neuropeptides: enkephalin, neuropeptide S, dalargin, orexin, vasopressin, leptin, cholecystokinin, dynorphin, detorphin I, oxytocin, vancomycin, gentamicin, tobramycin and doxycycline.

A lipophilic prodrug, palmitoylated Leucine[5]-Enkephalin (TPLENK), comprising a cleavable ester bond susceptible to blood esterases is an example of a lipophilic derivative of a hydrophilic drug which can be used in this invention.

The amphiphile compounds used in this invention are compounds comprising a hydrophobic moiety covalently linked to a hydrophilic moiety and are typically selected from the following compounds: sorbitan esters, polysorbates, poly(ethylene glycol)alkyl, aryl and cholesterol ethers [e.g. phenolic and alkyl derivatives of poly(ethylene glycol)], poly(ethylene oxide)-poly(propylene oxide) block copolymers, polymer amphiphiles, phospholipids, fatty acid salts, acylated amino acids, alkyl quaternary amine salts, alkyl amine oxides, alkyl sulphonates, aryl sulphonates, $C_4$-$C_{30}$ alkyl amine salts. Preferably, the amphiphile compound is an amphiphilic carbohydrate compound.

The amphiphilic carbohydrate compound is typically selected from chitosans, dextrans, alginic acids, starches, guar gums, and their derivatives. Preferably the amphiphilic compound is a chitosan.

In a preferred embodiment of the invention, the amphiphilic carbohydrate compound is represented by the formula:

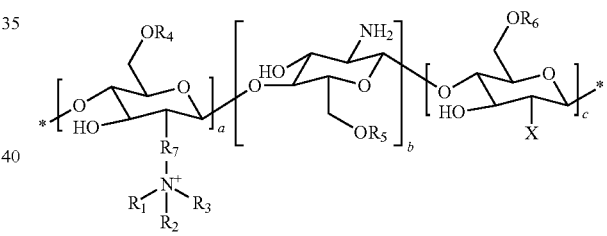

wherein a+b+c=1.000 and
a is between 0.01 and 0.990,
b is between 0.000 and 0.980, and
c is between 0.01 and 0.990;
and wherein:
X is a hydrophobic group;
$R_1$, $R_2$ and $R_3$ are independently selected from hydrogen or a substituted or unsubstituted alkyl group;
$R_4$, $R_5$ and $R_6$ are independently selected from hydrogen, a substituted or unsubstituted alkyl group, a substituted or unsubstituted ether group, or a substituted or unsubstituted alkene group;
$R_7$ may be present or absent and, when present, is an unsubstituted or substituted alkyl group, an unsubstituted or substituted amine group or an amide group;
or a salt thereof.

In the above general formula, the a, b and c units may be arranged in any order and may be ordered, partially ordered or random. The * in the formula is used to indicate the continuing polymer chain. In preferred embodiments, the molar proportion of the c units is greater than 0.01, and more preferably is at least 0.110, more preferably is at least 0.120, more preferably is at least 0.150 or in some embodiments is at least 0.18. Generally, the molar proportion of the c unit is 0.400 or less, and more preferably is 0.350 or less.

Preferably, the molar proportion of the a unit is between 0.010 and 0.800, and more preferably between 0.050 and 0.300.

Preferably, the molar proportion of the b unit is between 0.200 and 0.850, and more preferably between 0.200 and 0.750.

As can be seen from the above formula, the b units may optionally be absent. The c units provide the first portion of the monomer units that are derivatised with a hydrophobic group, and the a units provide the second portion of the monomer units and are derivatised with a quaternary nitrogen group. When present, the b units provide the third group of monomer units in which the amine groups are derivatised in a different manner to the first or second group, or else are underivatised.

In the present invention, the hydrophobic group X is preferably selected from a substituted or unsubstituted group which is an alkyl group such as a $C_{4-30}$ alkyl group, an alkenyl group such as a $C_{4-30}$ alkenyl group, an alkynyl group such as a $C_{4-30}$ alkynyl group, an aryl group such as a $C_{5-20}$ aryl group, a multicycle hydrophobic group with more than one $C_4$-$C_8$ ring structure such as a sterol (e.g. cholesterol), a multicyclic hydrophobic group with more than one $C_4$-$C_8$ heteroatom ring structure, a polyoxa $C_1$-$C_4$ alkylene group such as polyoxa butylene polymer, or a hydrophobic polymeric substituent such as a poly(lactic acid) group, a poly(lactide-co-glycolide) group or a poly(glycolic acid) group. The X groups may be linear, branched or cyclo groups. Any of the X groups may be directly linked to the c unit (i.e. at the C2 of the monomer unit), or via a functional group such as an amine group, an acyl group, or an amide group, thereby forming linkages that may be represented as X'-ring, X'—NH—, X'—CO-ring, X'CONH-ring, where X' is the hydrophobic group as defined above.

Preferred examples of X groups include those represented by the formulae $CH_3(CH_2)_n$—CO—NH— or $CH_3(CH_2)_n$—NH— or the alkeneoic acid $CH_3$ $(CH_2)_p$—CH=CH—$(CH_2)_q$—CO—NH—, where n is between 4 and 30, and more preferably between 6 and 20, and p and q may be the same or different and are between 4 and 16, and more preferably 4 and 14. A particularly preferred class of X substituents are linked to the chitosan monomer unit via an amide group, for example as represented by the formula $CH_3(CH_2)_n$ CO—NH—, where n is between 2 and 28. Examples of amide groups are produced by the coupling of carboxylic acids to the amine group of chitosan. Preferred examples are fatty acid derivatives $CH_3(CH_2)_n COOH$ such as those based on capric acid (n=8) lauric acid (n=10), myristic acid (n=12), palmitic acid (n=14), stearic acid (n =16) or arachidic acid (n=18).

In the above formula, $R_1$, $R_2$ and $R_3$ are preferably independently selected from hydrogen or a substituted or unsubstituted alkyl group such as a $C_{1-10}$ alkyl group. Where $R_1$, $R_2$ and/or $R_3$ are alkyl groups, they may be linear or branched. Preferably, $R_1$, $R_2$ and $R_3$ are independently selected from hydrogen, methyl, ethyl or propyl groups.

In the above formula, $R_4$, $R_5$ and $R_6$ present on the C6 or the sugar units are independently selected from hydrogen, a substituted or unsubstituted alkyl group, a substituted or unsubstituted ether group, or a substituted or unsubstituted alkene group. Preferred $R_4$, $R_5$ and $R_6$ groups are substituted with one of more hydroxyl groups, or another non-ionic hydrophilic substituent. Examples of $R_4$, $R_5$ and $R_6$ groups are represented by the formulae —$(CH_2)_p$—OH, where p is between 1 and 10, and is preferably between 2 and 4, or —$(CH_2)_p$—$CH_q(CH_2$—OH$)_r$ where p is between 1 and 10 and q is between 0 and 3 and r is between 1 and 3 and the sum of q+r=3, or —$(CH2)_p$—$C(CH_2$—OH$)_r$ where p is between 1 and 10, and r is 3, or —$(CH_2CH_2OH)_p$, where p is between 1 and 300.

The $R_7$ group may be present or absent in the general formula. When absent, it provides a quaternary ammonium functional group that is directly linked to the chitosan ring of the a monomer unit. When the $R_7$ group is present it may be a unsubstituted or substituted alkyl group (e.g. a $C_{1-10}$ alkyl group) for example as represented by the formula —$(CH_2)_n$—, an amine group as represented by the formula —NH—$(CH_2)_n$—, or an amide group as represented by the formula —NH—CO–$(CH_2)_n$—, where n is 1 to 10 and is preferably 1 to 4. A preferred example of the $R_7N^+R_1R_2R_3$ substituent is provided by coupling betaine (—OOC—$CH_2$—N—$(CH_3)_3$) to the amine substituent of the a unit providing an amide group such as in betaine, —NH—CO—$CH_2$—$N^+R_1R_2R_3$.

As indicated, some of the substituents described herein may be either unsubstituted or substituted with one or more additional substituent's as is well known to those skilled in the art. Examples of common substituent's include halo; hydroxyl; ether (e.g., $C_{1-7}$ alkoxy); formyl; acyl (e.g. $C_{1-7}$ alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$ alkylthio); sulphonic acid; sulfonate; sulphone; sulfonyloxy; sulfinyloxy; sulfamino; sulfonamino; sulfinamino; sulfamyl; sulfonamido; $C_{1-7}$ alkyl [including, e.g., unsubstituted $C_{1-7}$ alkyl, $C_{1-7}$ haloalkyl, $C_{1-7}$ hydroxyalkyl, $C_{1-7}$ carboxyalkyl, $C_{1-7}$ aminoalkyl, $C_{5-20}$ aryl, $C_{1-7}$ alkyl); $C_{3-20}$ heterocyclyl; and $C_{5-20}$ aryl (including, e.g., $C_{5-20}$ carboaryl, $C_{5-20}$ heteroaryl, $C_{1-7}$ alkyl-$C_{5-20}$ aryl and $C_{5-20}$ haloaryl)] groups.

The term "ring structure" as used herein, pertains to a closed ring of from 3 to 10 covalently linked atoms, yet more preferably 3 to 8 covalently linked atoms, yet more preferably 5 to 6 covalently linked atoms. A ring may be an alicyclic ring, or aromatic ring. The term "alicyclic ring," as used herein, pertains to a ring which is not an aromatic ring.

The term "carbocyclic ring", as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen or sulphur, though more commonly nitrogen, oxygen, or sulphur. Preferably, the heterocyclic ring has from 1 to 4 heteroatoms.

The above rings may be part of a "multicyclic group".

The compositions of the present invention may form particulate aggregates. These may be formed by the aggregation of individual amphiphile molecules and the lipophilic derivative of the hydrophilic drug and have a mean particle size between 20 nm and 20 µm. The mean particle size can readily be determined microscopically or by using photon correlation spectroscopy and is conveniently determined in aqueous dispersions prior to filtration. More preferably, the polymeric micellar aggregates have a minimum mean particle size of at least 100 nm, and more preferably at least 175 nm, and a maximum mean particle size which is preferably 10 µm or less. After filtration, the mean particle size typically reduces to a preferred range between about 100 nm and 500 nm.

Typically, the ratio of amphiphile compound to drug is within the range of 0.1-20:1; a preferred ratio is 1-10:1 and a more preferred ratio is around 5:1 by weight.

Typically, the ratio of amphiphile compound to drug to pharmaceutically acceptable carrier may be about 1-5 mg:1 mg:1 g.

The compositions may be delivered to the human or animal body by a range of delivery routes including, but not limited to: gastrointestinal delivery, including orally and per rectum; parenteral delivery, including injection, patches, creams etc; mucosal delivery, including nasal, inhalation and via pessary. In a preferred embodiment, the compositions are administered via parenteral, oral or topical routes and most preferably orally or by an intravenous route.

In addition to the lipophilic derivative of the hydrophilic drug and amphiphile as described above, the pharmaceutical compositions may comprise a pharmaceutically acceptable excipient, carrier, diluent, buffer, stabiliser or other materials well known to those skilled in the art. Such materials should be non-toxic and should not interfere with the efficacy of the composition. The precise nature of the carrier or other material may depend on the route of administration, e.g. parenteral, oral or topical routes.

Pharmaceutical compositions for oral administration may be in tablet, capsule, powder or liquid form. A tablet may include a solid carrier such as gelatine or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

When tablets are used for oral administration, typically used carriers include sucrose, lactose, mannitol, maltitol, dextran, corn starch, typical lubricants such as magnesium stearate, preservatives such as paraben, sorbin, anti-oxidants such as ascorbic acid, alpha-tocopherol, cysteine, disintegrators or binders. When administered orally as capsules, effective diluents include lactose and dry corn starch. Liquids for oral use include syrups, suspensions, solutions and emulsions, which may contain a typical inert diluent used in this field, such as water. In addition, the composition may contain sweetening and/or flavouring agents.

For intravenous, cutaneous or subcutaneous injection, or injection at the site of affliction, the composition will be in the form of parenterally acceptable aqueous solution which is pyrogen-free and has suitable pH, isotonicity and stability. Those of relevant skill in the art are well able to prepare suitable solutions using, for example, isotonic vehicles such as sodium chloride for injection. Preservatives, stabilisers, buffers, antioxidants and/or other additives may be included, as required.

A suitable daily dose can be determined based on age, body weight, administration time, administration method, etc. While the daily doses may vary depending on the condition and body weight of the patient, and the nature of the drug, a typical oral dose is about 0.1 mg-2 g/person/day, preferably 0.5-100 mg/person/day.

BRIEF DESCRIPTION OF THE DRAWINGS

The invention will now be illustrated by the following Examples, which refer to FIGS. 1-7, wherein.

EXAMPLES

Example 1

Peptide Synthesis

Peptide synthesis of Leucine[5]-Enkephalin-(tBu-tertiary butyl) (LENK-tBu) and of a novel lipidic Leucine[5]-Enkephalin analogue, Tyrosine Palmitate Leucine[5]-Enkephalin (TPLENK,) was carried out by standard solid phase methodology employing a Zinsser Analytic (U.K.) Raikin PS3 peptide synthesizer or manually. 9-fluorenylmethoxy carbonyl (FMOC) chemistry was used with dimethylformamide (DMF) as the solvent. All peptides were made on the pre-coupled with Leucine H$_2$N-Leu-2-Chlorotrityl resin. Stepwise addition of FMOC-orthogonically protected amino acid derivatives (four equivalents when synthesised using the peptide synthesizer and five equivalents when made manually) on the pre-coupled peptide support was employed with equivalent O-benzotriazole-N,N,N'N'-tetramethyl uranium hexafluoro phosphate (HBTU) in the presence of 4.45% N-methyl morpholine (NMM) (by volume) in dimethyl formamide (DMF). For manual synthesis each amino acid was coupled twice before proceeding to the next addition. The coupling steps were 45-min long employing HBTU as the coupling reagent and 25-min long when performed twice employing HBTU as a coupling reagent. Glycine was double-coupled.

For Leucine[5]-Enkephalin, FMOC deprotection was achieved with 20% (v/v) piperidine in DMF. The cleavage of the peptide from the resin (2-chlorotrityl resin) was achieved with acetic acid, trifluoroethanol, dichloromethane (AcOH/TFE/DCM-2:2:6) for 2 hours (Barlos et al. 1991) or utilising Reagent P [Phenol/trifluoroacetic acid (TFA) 5/95 (w/v)] for 2 hours at room temperature. If the tBu protection on tyrosine was required only the former cleavage mixture based on acetic acid was used, as TFA can also cleave the side-chain protecting group as well as the solid-support. Evaporation and removal of acetic acid as an azeotrope with hexane or evaporation of TFA resulted in reduced volume of a suspension containing the crude peptide. Then, the crude peptide (Leucine[5]-Enkephalin) was precipitated with (frozen, −20° C.) diethyl ether, collected with centrifugation (1500 rpm at 4° C. for 45 minutes) three times (with syringing and discarding the supernatant and further washing with frozen diethyl ether after the first two centrifugations), dried with nitrogen, dissolved in water and lyophilised. The overall yield of the reaction was between 92-99%.

Figure 1:
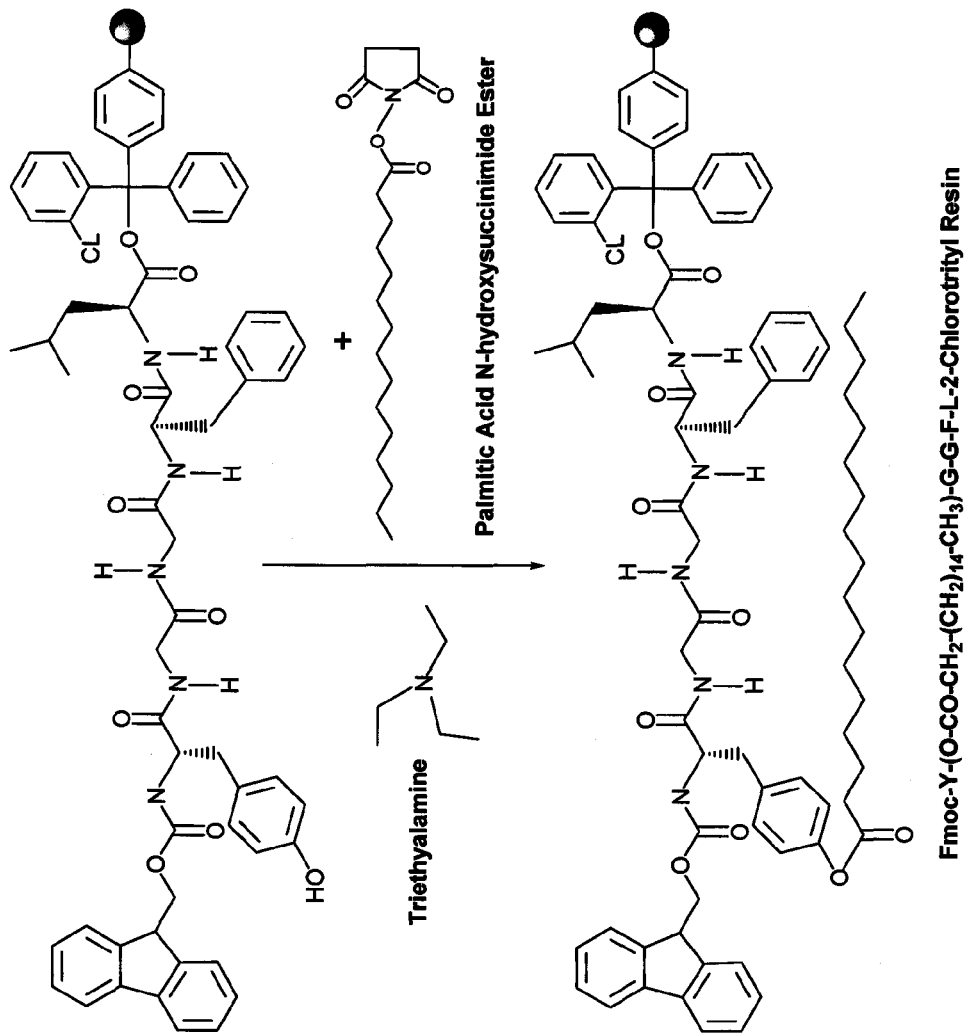
FIG. 1 shows palmitoylation of Fmoc protected Leucine[5]-Enkephalin using Palmitic acid N-Hydroxysuccinimide ester.

Triethylamine (350 μl, 2.5 mmol) was added to a solution of FMOC-Tyr-(OH)-Gly-Gly-Phe-Leu-2-Cl-Trt-Resin (0.1 mmol) in DMF (8 mL) and the resultant suspension was reacted with the N-hydroxysuccinimide ester of palmitic acid (176.75 mg, 0.5 mmol, PNS) in DMF (5 mL) at 25° C. (constant temperature room or water bath) for 24 h, during which time the suspension was agitated (120 rpm). The mixture was then concentrated in vacuo to remove volatile products and then was redissolved in DMF (4 mL). FIG. 1 illustrates the synthetic process. The redissolved product still on the resin was filtered and washed with copious amounts of DMF. The product bound to the resin was treated with 20% piperidine in DMF (20 mL) for 20-25 minutes. After washing with DMF and filtration, cleavage of the peptide chain from the resin was performed with the acetic acid cleavage mixture (AcOH/TFE/DCM-2:2:6) for 2 hours (Barlos et al. 1991) at room temperature as stated above. Then, the crude peptide (TPLENK) was precipitated with cold purified water (4° C., pH 7.0), collected with centrifugation (2500 rpm at 4° C. for 30 minutes) three times (with syringing and discarding the supernatant and further washing with cold water after the first two centrifugations) and lyophilised. The overall yield was between 55-75%.

FIG. 1 shows palmitoylation of Fmoc protected Leucine[5]-Enkephalin using PNS.

Peptide Purification:

Semi-preparative reverse-phase high performance liquid chromatography (RP-HPLC) was employed for the purification of the crude lyophilised Leucine[5]-Enkephalin and TPLENK. A Waters HPLC system comprising of a Waters TM 515 HPLC pump connected to a Water TM 717 plus Autosampler with a Jones Chromatography Column Heater Model 7971 and a Waters TM 486 Tunable Absorbance Detector was used. The peptides were eluted on a semi-preparative Waters Spherisorb ODS2 C18, 10×250 mm with a pore size of 10 μm with a flow rate of 4 ml min$^{-1}$ at 35° C. The mobile phase consisted of 82% 25 mM ammonium bicarbonate buffer and 18% acetonitrile. Unless otherwise indicated, samples were detected at 280 nm. The retention time was 7.1 minutes for Leucine[5]-Enkephalin and 8.3 minutes for TPLENK.

Peptide Characterisation:

The peptides were characterised by Electrospray ionisation (positive/negative) mass spectrometry, analytical reverse phase HPLC, nuclear magnetic resonance (NMR) spectrometry, Fourier transform infra-red (FTIR) spectroscopy, X-ray powder diffraction, transmission electron microscopy and photon correlation spectroscopy.

Example 2

Synthesis of Quaternary Ammonium Palmitoyl Glycol Chitosan (GCPQ)

Figure 2:
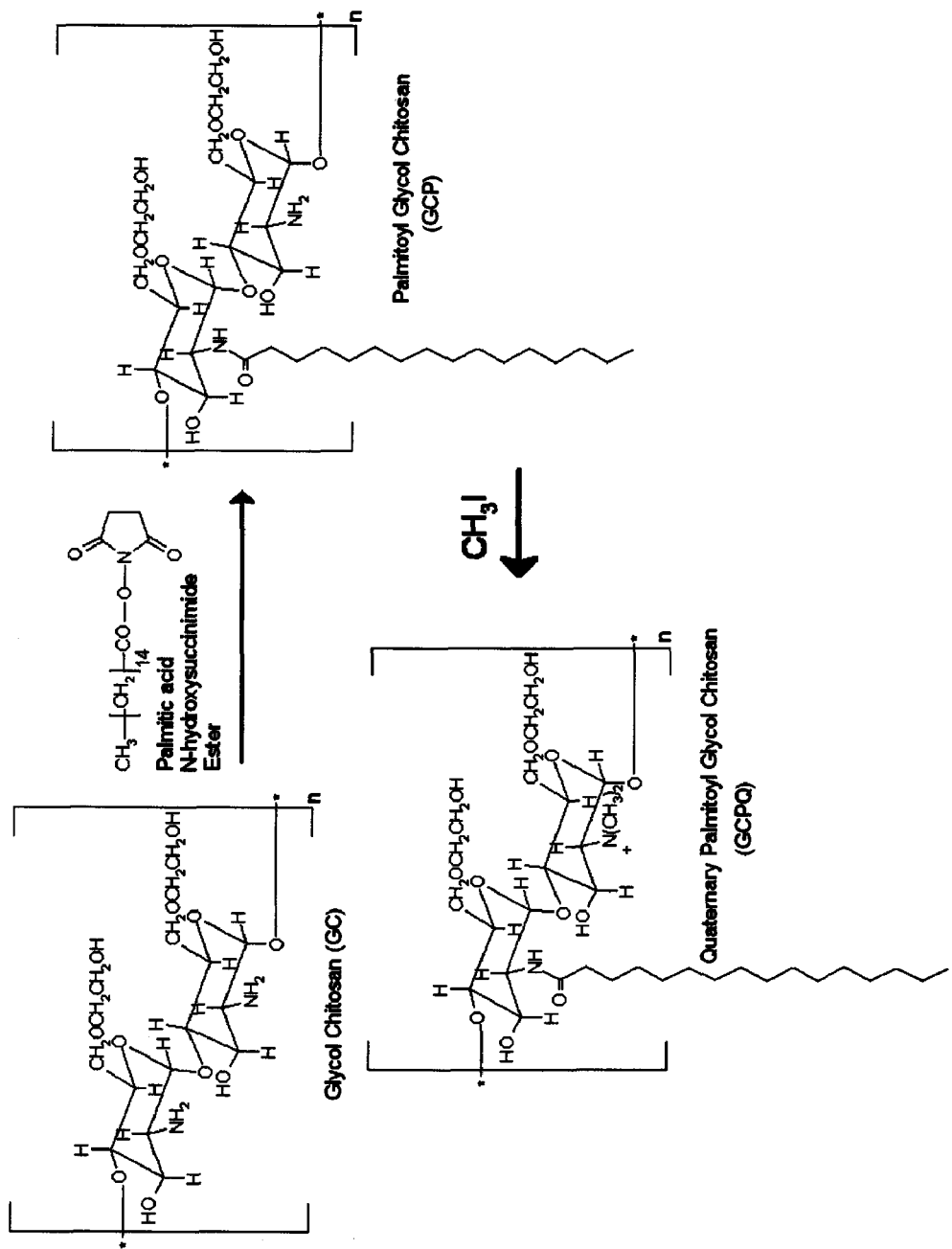
FIG. 2 shows a synthetic scheme for Quaternary ammonium Palmitoyl Glycol Chitosan.

A schematic representation of the synthetic pathway is illustrated in FIG. 2 which shows a synthetic scheme for quaternary ammonium palmitoyl glycol chitosan.

Acid Degradation of Glycol Chitosan

The acid degradation of glycol chitosan was carried out as described earlier (Wang et al. 2001). Glycol chitosan (2 g) was dissolved in hydrochloric acid (4M, 150 mL) and the solution filtered to remove insoluble impurities (if required). The (filtered) solution was placed in a preheated water bath at 50° C. At 24 hours the reaction was stopped and the product was removed from the water bath. Molecular weight was controlled by degradation time, i.e. increasing the acid degradation time decreased the molecular weight of the resulting polymer. Previous work has shown that a molecular weight of 26,000 Da was obtained after 24 hours of acid hydrolysis of glycol chitosan with a starting molecular weight of approximately 250,000 Da (Wang et al. 2001). The product was purified by exhaustively dialysing (Visking seamless cellulose tubing, molecular weight cutoff of 12,000-14,000 Da) against deionised water (5 L) with six changes over 24 hours. The dialysate at the end of the dialysis procedure (neutral pH) was subsequently freeze-dried, and the product was recovered as a cream-colored cotton-wool-like material. The degradation yielded 1.06 g (i.e. 53%) of degraded glycol chitosan.

Palmitoylation of Degraded Glycol Chitosan

The synthesis of palmitoyl glycol chitosan was carried out as described earlier (Qu et al. 2006). Briefly, degraded glycol chitosan (500 mg) and sodium bicarbonate (376 mg, ~0.045M) were dissolved in a mixture of absolute ethanol (24 mL) and deionised water (76 mL). To this glycol chitosan solution was added dropwise a solution of PNS (792 mg, ~2.24 mmole) dissolved in absolute ethanol (150 mL), with continuous stirring over a period of 1 hour. The mixture was then stirred for 72 hours and the product isolated by evaporating off most of the ethanol and extracting 3 times the remaining aqueous phase (~100 mL) with diethylether (each time twice the volume of the aqueous phase i.e. 200 mL was used). The aqueous mixture of the polymer was exhaustively dialysed (Visking seamless cellulose tubing, molecular weight cutoff 12-14,000 Da) against deionised water (5 L) with 6 changes over a 24-hour period and the resultant product freeze-dried to give a white cotton-like solid.

Quaternisation of Palmitoyl Glycol Chitosan

Quaternisation was carried out using essentially the same method as reported by Domard and others (Domard et al. 1986; Uchegbu et al. 2001) with modifications (Qu et al. 2006). Briefly palmitoyl glycol chitosan (300 mg) was dispersed in N-methyl-2-pyrrolidone (25 mL) overnight for 12 hours at room temperature. Sodium hydroxide (40 mg, 1 mmole as an aqueous solution 0.057M), methyl iodide (1.0 g, d: 1.275 g mL$^{-1}$, ~0.44 mL) and sodium iodide (45 mg, as an ethanolic solution ~0.05M) were added and the reaction stirred under a stream of nitrogen at 36° C. for 3 hours.

The quaternary ammonium product was precipitated with diethyl ether (400 mL), filtered and washed twice more with copious amounts of diethyl ether (twice with 300 mL) to give a light brown hygroscopic solid. The quaternised product was dissolved in water (100 ml) to give a yellow solution. The resultant solution was exhaustively dialysed against water (5 L) with six changes over a 24 h period and the dialysate was passed through a column (1×6 cm) packed with Amberlite IRA-96 Cl$^{-1}$. The column was packed with one volume of the resin (30 mL) and subsequently washed with hydrochloric acid solution (90 mL, 1M) followed by deionised water (10 L) to give a neutral pH. The clear eluate from the column was freeze-dried to give quaternary ammonium palmitoyl glycol chitosan (GCPQ) as a transparent fibrous solid. The synthetic yield of GCPQ is between 115-134 mg (i.e. 38.3-44.6%).

Example 3

Preparation of Self Assembled Polymer Nanoparticles

Preparation of Self Assembled Polymer Nanoparticles Without Drug

Self assembled polymer amphiphiles were prepared by vortexing (WhirliMixer, Fisherbrand) of GCPQ (2.3 mg or 5 mg) in double-deionised water (1 mL) and then by probe sonicating (MSE Soniprep 150) with the instrument set at 50% of its maximum output for 8 minutes on ice. Particle size was measured by Photon correlation spectroscopy (Malvern Zetasizer 3000HS$_A$, Malvern Instruments, UK) at 25° C. at a wavelength of 633 nm and the data analysed using the Contin method of data analysis. Polymer solutions were left for 15 min at room temperature (25° C.) before particle sizing was done. The clear dispersions were then syringe-filtered (0.45 μm, 33 mm Millex GP syringe driven filter unit, PES membrane for sterilisation of aqueous solutions) and the filtered solution was then measured again as above. Measurements were performed in triplicate.

The morphological examination of the nanoparticles was studied with TEM. A drop of unfiltered solution was placed on Formvar©/Carbon Coated Grid (F196/100 3.05 mm, Mesh 300, Tab Labs Ltd, England). Excess sample was filtered off with No. 1 Whatman Filter paper and negatively stained with 1% aqueous Uranyl Acetate. Imaging was carried out under a FEI (Ex. Philips) CM120 BioTwin Transmission Electron Microscope (TEM). Digital Images were captured using an AMT (digital) camera.

Polymer nanoparticles (unfiltered) presented a spherical morphology.

Preparation of Self Assembled Polymer NanoParticles (with Drug) for Oral Administration Polymer dispersions (75 mg mL$^{-1}$) with Leucine[5]-Enkephalin (LENK) (15 mg mL$^{-1}$) or Palmitoylated Leucine[5]-Enkephalin (TPLENK) (15 mg mL$^{-1}$) were prepared by vortexing (WhirliMixer, Fisherbrand) for 5 minutes in double de-ionised filtered [0.2 μm, 33 mm Millex GP syringe driven filter unit, polyether sulphone (PES) membrane for sterilisation of aqueous solutions] water (pH 6.4), followed by probe sonication (MSE Soniprep 150) with the instrument set at 50% of its maximum output for 15 minutes on ice. Formulations were not filtered. The resulting particulate formulations were imaged using scanning electron microscopy (SEM). Fresh samples were mounted on a standard SEM sample holder and were fixed on a brass/aluminium stub using double sided carbon impregnated adhesive discs. The sample was then sputter coated with a conducting gold-palladium (10 nm, 60% gold-palladium) coating using a SEM coating system for 2 minutes at 30 mA (Emitech K550 Sputter Coater, Emitech Limited, Ashford, UK, Deposition range: 0-50 mA, Deposition rate: 0-25 nm min$^{-1}$, Sputter timer: 0-4 min, Vacuum Pump: 85 lit min$^{-1}$, room temperature) before viewed and photographed under a range of magnifications under high vacuum using Philips XL 30 ESEM FEG scanning electron microscope.

Preparation of Self Assembled Polymer NanoParticles (with Drug) for Intravenous Administration Polymer dispersions (6.9 or 11.5 mg mL$^{-1}$) with Leucine[5]-Enkephalin (LENK) (3 or 5 mg mL$^{-1}$) or Palmitoylated Leucine[5]-Enkephalin (TPLENK) (3 mg mL$^{-1}$) were prepared by vortexing (WhirliMixer, Fisherbrand) for 5 minutes in phosphate buffered saline (pH 7.4), followed by probe sonication (MSE Soniprep 150) with the instrument set at 50% of its maximum output for 15 minutes on ice. The formulations were left overnight in the fridge and prior to intravenous administration were filtered (0.8 μm, 13 mm, Acrodisc Syringe Filter, Super Low Protein Binding Non-Pyrogenic Membrane, PALL Life Sciences). A clear filtrate was obtained for Leucine[5]-Enkephalin and Leucine[5]-Enkephalin and GCPQ and a translucent liquid was obtained for Palmitoylated Leucine[5]-Enkephalin (TPLENK) and GCPQ. The administered intravenous volume of the formulations was set to a maximum of 0.2 ml per mouse. The administered volume was adjusted based on HPLC quantification of Leucine[5]-Enkephalin and TPLENK after filtration and the body weight of each animal. The maximum volume was dosed for placebo (NaCl, 0.9% w/v) receiving mice.

Particle size of the filtered formulations was measured by Photon correlation spectroscopy (Malvern Zetasizer 3000HS$_A$, Malvern Instruments, UK) at 25° C. at a wavelength of 633 nm and the data analysed using the Contin method of data analysis. Polymer dispersions were left for 15 min at room temperature (25° C.) before particle sizing was done. Measurements were performed in triplicate.

The morphological examination of the nanoparticles was studied with TEM. A drop of the filtered formulations was placed on Formvar©/Carbon Coated Grid (F196/100 3.05 mm, Mesh 300, Tab Labs Ltd, England). Excess sample was filtered off with No. 1 Whatman Filter paper and negatively stained with 1% aqueous Uranyl Acetate. Imaging was carried out under a FEI (Ex. Philips) CM120 BioTwin Transmission Electron Microscope (TEM). Digital Images were captured using an AMT (digital) camera.

Polymer nanoparticles (unfiltered) presented a spherical morphology.

Analysis of Peptide/Drug Loaded Polymers

Polymer dispersions with Leucine[5]-Enkephalin (LENK) or Palmitoylated Leucine[5]-Enkephalin (TPLENK) were dissolved in mobile phase and analysed by HPLC. Samples were chromatographed over a reverse phase HPLC Sunfire C18 column (5 μm, 4.6 mm×250 mm) with a guard column attached [Waters Sunfire C18 (5 μm, 4.6 mm×10 mm)], using a Waters TM 515 HPLC pump connected to a Water TM 717 plus Autosampler with a Waters TM 486 Tunable Absorbance Detector. The mobile phase consisted of 82% 50 mM acetate buffer and 18% acetonitrile (pH 5.8). Unless otherwise indicated, samples were detected at 280 nm. The flow rate was set at 1 mL min$^{-1}$ at 35° C. and an injection volume of 40 μL was used. The retention time was 11.5 minutes for Leucine[5]-Enkephalin and 14.0 minutes for TPLENK and the lowest detection limits were 1 μg mL$^{-1}$ and 10 μg mL$^{-1}$ for Leucine[5]-Enkephalin and TPLENK respectively. Empower software I was used for data analysis.

Results for Peptide/drug Loaded Polymer Dispersions for Oral Administration

Drug—Polymer dispersions presented as a viscous particulate formulation and the drug content was analysed at 99-100% of the initial amount added.

Results for Peptide/drug Loaded Polymer Dispersions for Intravenous Administration Drug—Polymer dispersions presented as a clear or translucent particulate formulations and the drug content was analysed at 40-98% of the initial amount added depending on the formulation.

Example 4

In Vivo Studies—Oral Administration

Pharmacokinetics—Animals

ICR (CD-1) male out bred mice (18-24 g, 4 weeks old, Harlan, Oxon, UK) were used. The animals were housed in groups of 5 in plastic cages in controlled laboratory conditions with ambient temperature and humidity maintained at ~22° C. and 60% with a 12-hour light and dark cycle (lights on at 7:00 and off at 19:00). Food and water were available ad libitum and the animals acclimatised for 5-7 days prior to any experiments in the Animal House, School of Pharmacy, University of London (London, UK). Animals were fasted overnight for oral delivery experiments. Animals were only used once and were acclimatised at the testing environment for at least 1 hour prior to testing. All experiments were performed in accordance with the recommendations and policies of the Home Office (Animals Scientific Procedures Act 1986, UK) and the Ethics Committee of the School of Pharmacy, University of London guidelines for the care and use of laboratory animals.

Syringes were attached to 19-20 G commercial gavage needles (2-3 cm long) for oral administration.

Formulations

These studies included a combination of the following arms: (i) Placebo: $H_2O$, (ii) Leucine[5]-Enkephalin (L), (iii) Leucine[5]-Enkephalin and GCPQ (LG) and (iv) Palmitate Tyrosyl Leucine[5]-Enkephalin (TPLENK) and GCPQ (PG). The dose administered corresponded to 70 mg $Kg^{-1}$ and 100 mg $Kg^{-1}$ for Leucine[5]-Enkephalin (L and LG) and PTLENK (PG) respectively. Double de-ionised filtered (0.2 μm, 33 mm Millex GP syringe driven filter unit, PES membrane for sterilisation of aqueous solutions) water was used as the disperse phase for the oral formulations. Final formulation concentration of Leucine[5]-Enkephalin was 15 mg $mL^{-1}$ with a ratio of peptide to polymer 1:5 w/w. All formulations were prepared by vortexing (WhirliMixer, Fisherbrand) and then by probe sonication (MSE Soniprep 150) with the instrument set at 50% of its maximum output for 15 minutes on ice. The formulations were left overnight in the fridge; the administered volume was set to a maximum of 0.2 ml per mouse. The administered volume was adjusted based on the HPLC quantification of LENK and TPLENK and the body weight of each animal. The maximum volume was dosed for placebo ($H_2O$) receiving mice.

Examination of the oral particulate formulations was done with scanning electron microscopy (SEM). Fresh samples were fixed on a brass/aluminium stub, sputter-coated with gold (10 nm, 60% gold-palladium) and viewed under high vacuum using a Phillips XL 30 ESEM FEG scanning electron microscope.

HPLC Quantification

The peptides were analysed by reversed phase high-performance liquid chromatography on a reversed phase Waters Sunfire C18 column (5 μm, 4.6 mm×250 mm) with a guard column attached [Waters Sunfire C18 (5 μm, 4.6 mm×10 mm)], using a Waters TM 515 HPLC pump connected to a Water TM 717 plus Autosampler with a Waters TM 486 Tunable Absorbance Detector. The mobile phase consisted of 82% 50 mM acetate buffer and 18% acetonitrile (pH 5.8). Unless otherwise indicated, samples were detected at 280 nm. The flow rate was set at 1 mL $min^-$ at 35° C. for analytical runs and the injection volume at 40 μL. The retention time was 11.5 minutes for Leucine[5]-Enkephalin and 14.0 minutes for TPLENK and the lowest detection limits were 1 μg $mL^{-1}$ and 10 μg $mL^{-1}$ for Leucine[5]-Enkephalin and TPLENK respectively. Empower software I was used for data analysis.

Samole Handling and Extraction

Blood samples (0.4-0.8 mls per mouse) were collected into a chilled syringe and transferred into evacuated sterile spray coated (with tripotassium ethylenediamine tetraacetic acid—3.6 mg) medical grade PET tubes (3×75 mm K3E Vacutainer©, BD Biosciences, UK) and maintained on ice (4° C.) until centrifugation. There is no dilution effect in spray coated tubes. Plasma was obtained as the supernatant after centrifugation of blood samples at 1,600 g or 4800 rpm for 15 minutes at 4° C. with a Hermle Z323 centrifuge (Hermle Laborteschink GmbH, Germany) and was pipetted into 1.5 mL centrifuge tubes and stored at −70° C. for later use.

Brain tissue minus the cerebellum (0.25-0.35 g) recovered from mice was immediately frozen in liquid nitrogen (−80° C.) until they were homogenised. The brain weight was recorded for each individual animal. After thawing tissues were boiled for 10 minutes in 30 volumes of a mixture of 1M of acetic acid, 0.02M of hydrochloric acid and 0.1% 2-mercaptoethanol (De Ceballos et al. 1991; Ahmed et al. 1994; Wu et al. 2005). The tissues were homogenised with 80 strokes per minute for half a minute with a glass 3 mL homogeniser (Jencons-PLS, England). The homogenate was transferred in 15 mL centrifuge tubes and was centrifuged to remove any debris at 9,000 rpm for 20 minutes at 4° C. with a Hermle Z323 centrifuge (Hermle Laborteschink GmbH, Germany). The pellet was discarded and the supernatant stored in glass 14 mL vials was frozen (−20° C.) and lyophilised. The lyophilised samples were stored at −80° C. for later use.

The lyophilised brain homogenate samples were reconstituted with 1 mL of Reagent A (1% Trifluoroacetic acid) vortexed and centrifuged at 13,000 rpm for 20 minutes (MicroCentaur, MSE, London, UK). 100 μL of plasma after thawing and 100 μL of Reagent A were centrifuged at 13,000 rpm for 20 minutes (MicroCentaur, MSE, London, UK) to acidify the plasma sample and remove interfering proteins. C18 silica solid phase extraction columns (Waters SEP-PAK, 200 mg C18, Bachem, UK) were equilibrated with 1 mL of Reagent B (60% Acetonitrile, 1% Trifluoroacetic acid and 39% distilled water) and washed with 9 mL of Reagent A. 300 μL of the supernatant of the reconstituted brain homogenate and the supernatant of the plasma without the pellet were loaded onto the equilibrated column. Then, the columns were washed with 6 mL of Reagent A and the washings were discarded. The peptides were eluted with 3 mL of Reagent B and collected in a 5 mL polypropylene tube. The eluates were dried under a stream of Nitrogen at 30° C. using a sample concentrator (Dri-Block DB-3, Techne Sample Concentrator). The samples were then kept at −20° C. until they were used for RIA quantification.

Radioimmunoassay

Quantification of the amount of Leucine[5]-Enkephalin was according to the manufacturer's protocol (S-2118, Bachem, UK). The kit is based on the principle of competitive radioimmunoassay and it is 100% specific for Leucine[5]-Enkephalin.

Results

HPLC quantification of the peptide content of the formulations was for L, LG and PG for oral administration 99.9%, 99.1% and 98.9% respectively.

The pharmacokinetics of L, LG, PG following oral administration were studied in mice. Molar equivalent doses (Leucine[5]-Enkephalin) of TPLENK and Leucine[5]-Enkephalin were used for the studies. Since the original radioimmunoassay was developed specifically for Leucine[5]-Enkephalin, when analysing TPLENK samples only the amount of TPLENK bioconverted in vivo to Leucine[5]-Enkephalin was quantified.

Figure 3:
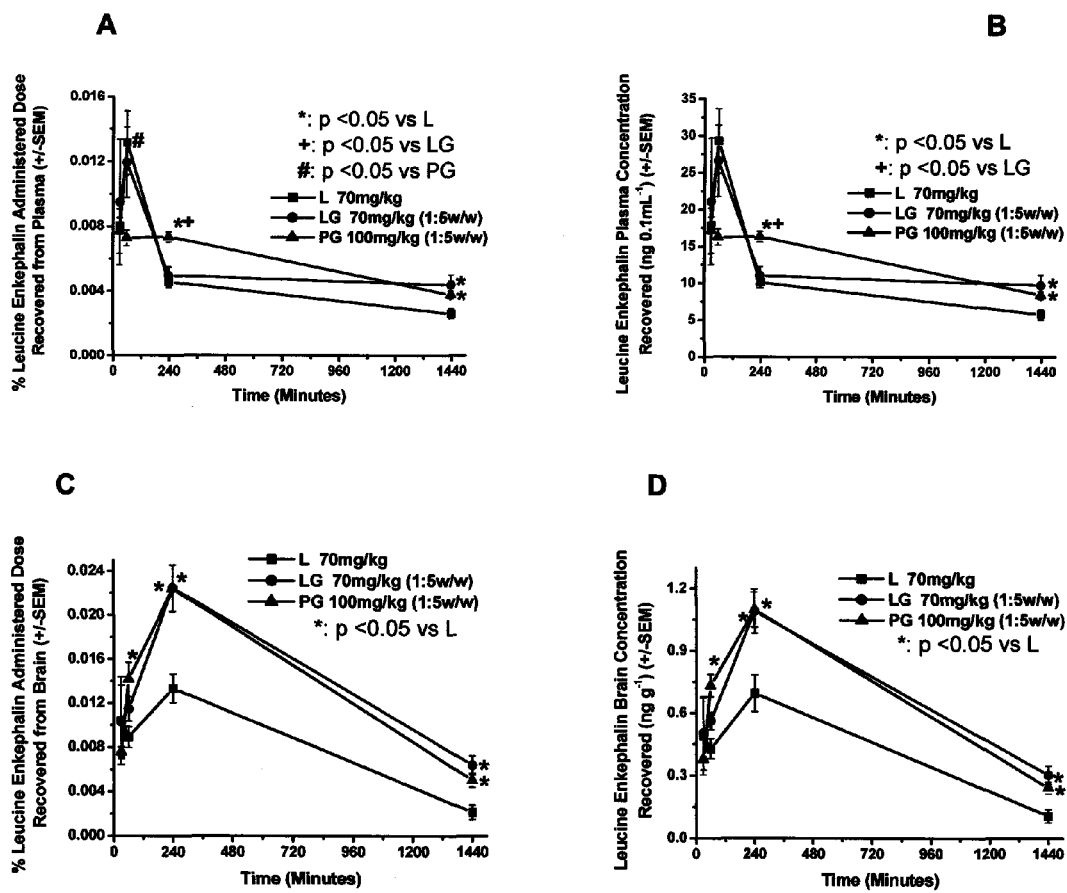
FIG. 3 shows the in vivo concentration of Leucine[5]-Enkephalin following oral administration.

The plasma concentration of Leucine[5]-Enkephalin following oral administration peaked at 1 hour for L and LG formulations (L: 29.3 ng $10^{-1}$ $mL^{-1}$ and LG: 26.6 ng $10^{-1}$ $mL^{-1}$) and 30 minutes for PG (17.1 ng $10^{-1}$ $mL^-$) and at 4 hours in the brain tissue for all three formulations (L: 0.695 ng $g^{-1}$, LG: 1.090 ng $g^{-1}$, PG: 1.098 ng $g^{-1}$). The AUC (0-1440) in the brain increased by 1.7 fold for both nanoparticulate formulations (LG and PG) when compared to levels obtained with Leucine[5]-Enkephalin alone. Statistically significant plasma and brain levels were achieved: for the nanoparticulate formulation of the lipidic peptide (PG) versus Leucine[5]-Enkephalin alone at 4 hours (p=0.001) in the plasma and 1 hour (p=0.006), 4 hours (p=0.017) and 24 hours (p=0.019) in the brain and versus LG at 4 hours (p=0.013) in the plasma; for the nanoparticulate formulation of Leucine[5]-Enkephalin (LG) when compared to Leucine[5]-Enkephalin alone at 4 hours (p=0.030) and 24 hours (p=0.013) in the brain. These results are shown in FIG. 3. No Leucine[5]-Enkephalin was detected in samples taken from animals receiving an oral dose of water.

Example 5

Pharmacodynamics—Oral Administration

Leucine[5]-Enkephalin causes central analgesic effects in the brain with slight preference for δ-opioid receptor. Occurrence of central analgesic effects would prove the brain targeting of Leucine[5]-Enkephalin-GCPQ particulate formulations and TPLENK-GCPQ particulate formulations in accordance with the preliminary pharmacokinetic data. Leucine[5]-Enkephalin and water have been used as controls. Leucine[5]-Enkephalin alone was used in order to observe the equipotent effect of this peptide in the same dose as in the particulate formulation and water as a placebo to rule out the plausible effects of endogenously produced neuropeptides during antinociception testing.

Animals

ICR (CD-1) male out bred mice (22-28 g, 4-5 weeks old, Harlan, Oxon, UK) were used. The animals were housed in groups of 5 in plastic cages in controlled laboratory conditions with ambient temperature and humidity maintained at ~22° C. and 60% with a 12-hour light and dark cycle (lights on at 8:00 and off at 20:00). Food and water were available ad libitum and the animals acclimatised for 5-7 days, prior to any experiments, in the Animal House, School of Pharmacy, University of London (London, UK). Animals were fasted overnight for oral delivery experiments. Animals were only used once and were acclimatised at the testing environment for at least 20 hours prior to testing. All testing was performed in accordance with the recommendations and policies of the Home Office (Animals Scientific Procedures Act 1986, UK) and the Ethics Committee of the School of Pharmacy, University of London guidelines for the care and use of laboratory animals.

Syringes were attached to 19-20 G commercial gavage needles (2-3 cm long) for oral administration.

Formulations

This study included four arms: (i) Placebo: $H_2O$, (ii) Leucine[5]-Enkephalin (L), (iii) Leucine[5]-Enkephalin and GCPQ (LG) and (iv) Palmitate Tyrosyl Leucine[5]-Enkephalin (TPLENK) and GCPQ (PG). The dose administered corresponded to 70 mg $Kg^{-1}$ and 100 mg $Kg^{-1}$ after oral gavage for Leucine[5]-Enkephalin (L and LG) and TPLENK (PG) respectively. Double de-ionised filtered (0.2 μm, 33 mm Millex GP syringe driven filter unit, PES membrane for sterilisation of aqueous solutions) water was used as the disperse phase. The final formulation concentration of both peptides was 15 mg $mL^{-1}$ with a ratio of peptide to polymer of 1:5 w/w. All formulations were prepared by vortexing (WhirliMixer, Fisherbrand) and then by probe sonication (MSE Soniprep 150) with the instrument set at 50% of its maximum output for 15 minutes on ice. The formulations were left overnight in the fridge. The administered volume was set to a maximum of 0.2 ml per mouse. The administered volume was adjusted based on HPLC quantification of LENK and TPLENK and the body weight of each animal. The maximum volume was dosed for placebo ($H_2O$) receiving mice.

Antinociception Studies

Antinociception was assessed in mice using the tail flick warm water bioassay (D'Amour and Smith 1941; Mogil et al. 1999). The protruding distal half of the tail (4-5 cm) of confined mice in a Plexiglas restrainer was immersed in circulating warm water maintained at 55° C.±0.1° C. (Tjolsen and Hole 1993; Polt et al. 1994) by a thermostatically controlled water bath (W14, Grant Instruments, Cambridge Ltd, Herts, UK). Before any experiment was performed the temperature was checked using a thermometer (Gallenkamp, Griffin, THL-333-020 L, 76 mm×1 mm, UK). The response latency times, in centiseconds, recorded for each mouse to withdraw its tail by a "sharp flick" were recorded using a digital stopwatch capable of measuring 1/100th of a second. The first sign of a rapid tail flick was taken as the behavioural endpoint which followed in most cases 1-3 slow tail movements. Three separate withdrawal latency determinations (separated by ≧20 sec) were averaged (Polt et al. 1994) and individual time points were at least 10 minutes apart. The tails of the mice were wiped dry immediately after testing to prevent the hot water from clinging to the tail producing erythema. Mice not responding within 5 sec were excluded from further testing (Baseline cut-off=5 seconds) and the baseline latency was measured for all mice 2 hours prior testing. Maximum possible cut-off was set to 10 seconds to avoid unnecessary damage to the tail (Tjolsen and Hole 1993). A maximum score was assigned (100%) to animals not responding within 10 seconds. The response times were then converted to percentage of maximum possible effect (% MPE) by a method reported previously (Polt et al. 1994). Briefly, percent antinociception was calculated as 100%×(test latency-baseline latency)/(10 seconds−baseline latency). Data are presented as the mean±SEM for groups of 16 mice per arm of oral delivery studies. Data are also presented in the quantal form of the tail flick test (number of mice that exhibited maximum latencies to thermal stimuli) which ensures no false positive responses (D'Amour and Smith 1941). An analgesic responder was defined as one whose response tail flick latency was two or more times the value of the baseline latency (Shimoyama et al. 1997).

Statistical Analysis

All results were expressed as mean±standard error (i.e. SD/√n). A one-way ANOVA test using Minitab 16 was done to assess any statistical difference among the means of % MPE for the different arms of the study. A post-hoc analysis (Tukey's Test) was performed to determine the groups, which show significant difference. In each case, a p-value less than 0.05 was considered as a representation of a significant difference.

Oral Peptide Delivery Results

Average baseline latency was determined to be 2.33±0.70 (Mean±SD) sec. Maximal possible latencies were reached for none, one, six and nine mice out of 16 for $H_2O$ (0%), L (6.25%), LG (37.5%) and PG (56.25%) respectively. The number of analgesic responders (defined as one whose response was 2 or more times the value of the baseline latency) was none, five, thirteen and fifteen out of 16 for $H_2O$ (0%), L (31.25%), LG (81.25%) and PG (93.75%) respectively. Statistically significant differences (p <0.05) were observed between PG versus $H_2O$ (30, 60, 90, 120, 150, 180, 240, 360, 480 minutes, p=<0.0001 for all time points), PG versus L (90, 120, 150, 180, 240, 360, 480 minutes, p=<0.0001 for all time points), PG versus LG ( 60, 360, 480 minutes, p=<0.0001 at all time points), LG versus $H_2O$ (30, 90, 120, 150, 180 minutes, p=<0.0001 for all time points), and LG versus L (60, 360, 480 minutes, p=<0.001 for all time points)

Figure 4:
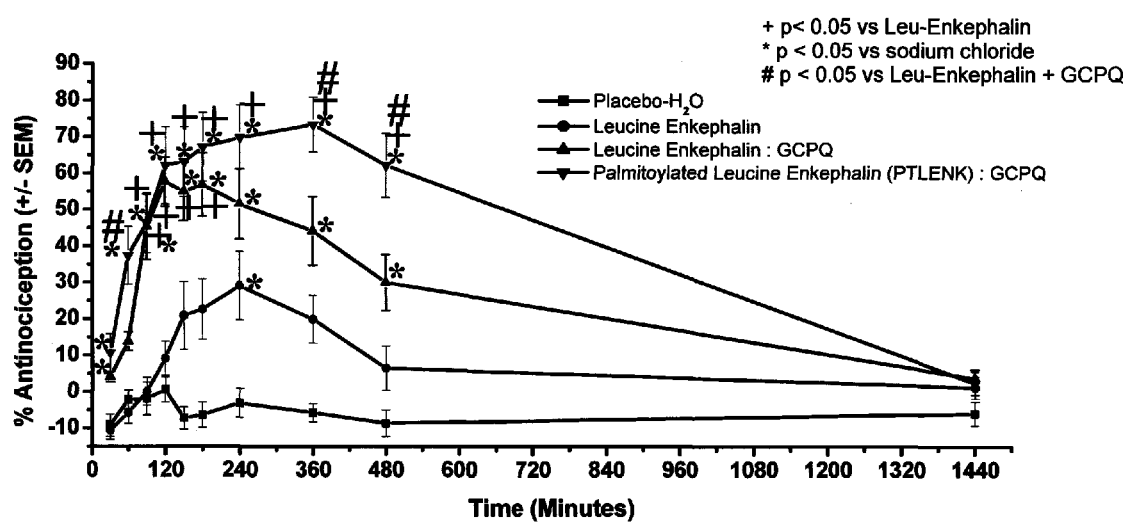
FIG. 4 shows the % antinociception at equivalent does of Leucine[5]-Enkephalin (70 mg kg$^{-1}$) after oral administration of Leucine[5]-Enkephalin to CD-1 mice (n=16)

FIG. 4 shows the % antinociception at equivalent doses after oral administration of the peptide formulations to the CD-1 mice (n=16). The ANOVA statistically different groups are: *: p<0.05 vs $H_2O$, +: p<0.05 vs Leucine[5]-Enkephalin, #: p <0.05 vs Leucine[5]-Enkephalin-GCPQ.

Example 6

In Vivo Studies—Intravenous Administration

Pharmacokinetics—Animals

ICR (CD-1) male out bred mice (18-24 g, 4 weeks old, Harlan, Oxon, UK) were used. The animals were housed in groups of 5 in plastic cages in controlled laboratory conditions with ambient temperature and humidity maintained at ~22° C. and 60% respectively with a 12-hour light and dark cycle (lights on at 7:00 and off at 19:00). Food and water were available ad libitum and the animals acclimatised for 5-7 days prior to any experiments in the Animal House, School of Pharmacy, University of London (London, UK). Animals were only used once and were acclimatised at the testing environment for at least 1 hour prior to testing. All experiments were performed in accordance with the recommendations and policies of the Home Office (Animals Scientific Procedures Act 1986, UK) and the Ethics Committee of the School of Pharmacy, University of London guidelines for the care and use of laboratory animals.

Syringes were attached to 26 G×⅝ inches (0.45 mm×16 mm, BD Microlance™ 3) for intravenous administration.

Formulations

These studies included a combination of the following arms: (i) Leucine[5]-Enkephalin and GCPQ (LG) and (ii) TPLENK and GCPQ (PG) and NaCL (0.9% w/v—placebo). The dose administered corresponded to 10 mg kg$^{-1}$ for Leucine[5]-Enkephalin (L and LG) and TPLENK (PG) and 8.9 and 12.75 mg kg$^{-1}$ for Leucine[5]-Enkephalin (L and LG) and TPLENK (PG) respectively. Sodium chloride 0.9% was used as the disperse phase. Final formulation concentration of Leucine[5]-Enkephalin was 5 or 3 mg mL$^{-1}$ with a ratio of peptide to polymer 1:2.3 w/w. All formulations were prepared by vortexing (WhirliMixer, Fisherbrand) and then by probe sonication (MSE Soniprep 150) with the instrument set at 50% of its maximum output for 15 minutes on ice. The formulations were left overnight in the fridge and prior to IV administration were filtered (0.8 μm, 13 mm, Acrodisc Syringe Filter, Supor Low Protein Binding Non-Polygenic Membrane, PALL Life Sciences). A clear filtrate was obtained for Leucine[5]-Enkephalin and Leucine[5]-Enkephalin and GCPQ and a translucent filtrate for TPLENK and GCPQ. The administered volume was adjusted based on the HPLC quantification of Leucine[5]-Enkephalin and TPLENK and the body weight of each animal. Administered volume was set to a maximum of 0.2 ml per mouse of formulations administered. The maximum volume was dosed for placebo (NaCl) receiving mice.

The particle size and distribution of freshly filtered polymer dispersions with Leucine[5]-Enkephalin (LENK) [3 or 5 mg mL$^{-1}$] or Palmitoylated Leucine[5]-Enkephalin (TPLENK) [3 mg mL$^{-1}$] prepared for IV pharmacokinetic and pharmacodynamic studies were determined by photon correlation spectroscopy (PCS) (Malvern Zetasizer 3000HS, Malvern Instruments, UK) at 25° C. at a wavelength of 633 nm and the data analysed using the Contin method of data analysis. Polymer dispersions were left for 30 min at room temperature (25° C.) before particle sizing was done.

The morphological examination of the nanoparticles was studied with transmission electron microscopy (TEM). A drop of the filtered intravenous formulations was placed on Formvar©/Carbon Coated Grid (F196/100 3.05 mm, Mesh 300, Tab Labs Ltd, England). Excess sample was filtered off with No. 1 Whatman Filter paper and negatively stained with 1% aqueous Uranyl Acetate. Imaging was carried out under a FEI CM120 BioTwin Transmission Electron Microscope (Ex. Philips, Eindhoven, Netherlands). Digital Images were captured using an AMT (digital) camera.

HPLC Quantification

The peptides were analysed by reversed phase high-performance liquid chromatography on a reversed phase Waters Sunfire C18 column (5 μm, 4.6 mm×250 mm) with a guard column attached [Waters Sunfire C18 (5 μm, 4.6 mm×10 mm)], using a Waters TM 515 HPLC pump connected to a Water TM 717 plus Autosampler with a Waters TM 486 Tunable Absorbance Detector. The mobile phase consisted of 82% 50 mM acetate buffer and 18% acetonitrile (pH 5.8). Unless otherwise indicated, samples were detected at 280 nm. The flow rate was set at 1 mL min$^{-1}$ at 35° C. for analytical runs and the injection volume at 40 μL. The retention time was 11.5 minutes for Leucine[5]-Enkephalin and 14.0 minutes for TPLENK and the lowest detection limits were 1 μg mL$^{-1}$ and 10 μg mL$^{-1}$ for Leucine[5]-Enkephalin and TPLENK respectively. Empower software I was used for data analysis.

Sample Handling and Extraction

Blood samples (0.4-0.8 mls per mouse) were collected into a chilled syringe and transferred into evacuated sterile spray coated (with tripotassium ethylenediamine tetraacetic acid—3.6 mg) medical grade PET tubes (3×75 mm K3E Vacutainer©, BD Biosciences, UK) and maintained on ice (4° C.) until centrifugation. There is no dilution effect in spray coated tubes. Plasma was obtained as the supernatant after centrifugation of blood samples at 1,600 g or 4800 rpm for 15 minutes at 4° C. with a Hermle Z323 centrifuge (Hermle Laborteschink GmbH, Germany) and was pipetted into 1.5 mL centrifuge tubes and stored at −70° C. for later use.

Brain tissue minus the cerebellum (0.25-0.35 g) recovered from mice was immediately frozen in liquid nitrogen (−80° C.) until they were homogenised. The brain weight was recorded for each individual animal. After thawing tissues were boiled for 10 minutes in 30 volumes of a mixture of 1M of acetic acid, 0.02M of hydrochloric acid and 0.1% 2-mercaptoethanol (De Ceballos et al. 1991; Ahmed et al. 1994; Wu et al. 2005). The tissues were homogenised with 80 strokes per minute for half a minute with a glass 3 mL homogeniser (Jencons-PLS, England). The homogenate was transferred in 15 mL centrifuge tubes and was centrifuged to remove any debris at 9,000 rpm for 20 minutes at 4° C. with a Hermle Z323 centrifuge (Hermle Laborteschink GmbH, Germany). The pellet was discarded and the supernatant stored in glass 14 mL vials was frozen (−20° C.) and lyophilised. The lyophilised samples were stored at −80° C. for later use.

The lyophilised brain homogenate samples were reconstituted with 1 mL of Reagent A (1% Trifluoroacetic acid) vortexed and centrifuged at 13,000 rpm for 20 minutes (MicroCentaur, MSE, London, UK). 100 μL of plasma after thawing and 100 μL of Reagent A were centrifuged at 13,000 rpm for 20 minutes (MicroCentaur, MSE, London, UK) to acidify the plasma sample and remove interfering proteins. C18 silica solid phase extraction columns (Waters SEP-PAK, 200 mg C18, Bachem, UK) were equilibrated with 1 mL of Reagent B (60% Acetonitrile, 1% Trifluoroacetic acid and 39% distilled water) and washed with 9 mL of Reagent A. 300 μL of the supernatant of the reconstituted brain homogenate and the supernatant of the plasma without the pellet were loaded onto the equilibrated column. Then, the columns were washed with 6 mL of Reagent A and the washings were discarded. The peptides were eluted with 3 mL of Reagent B and collected in a 5 mL polypropylene tube. The eluates were dried under a stream of Nitrogen at 30° C. using a sample concentrator (Dri-Block DB-3, Techne Sample Concentrator). The samples were then kept at −20° C. until they were used for RIA quantification.

Radioimmunoassay

Quantification of the amount of Leucine[5]-Enkephalin was according to the manufacturer's protocol (S-2118, Bachem, UK). The kit is based on the principle of competitive radioimmunoassay and it is 100% specific for Leucine[5]-Enkephalin.

Results

HPLC quantification of the peptide content of the formulations revealed that the peptide content for LG and PG formulations was 75-98% of the original amount for LG and 40-58% of the original amount for PG.

The pharmacokinetics of LG and PG following intravenous administration were studied in mice. When comparing Leucine[5]-Enkephalin with TPLENK, a molar equivalent dose of TPLENK was used for the studies. Since the original radioimmunoassay was developed specifically for Leucine[5]-Enkephalin, when analysing TPLENK samples only the amount of TPLENK bioconverted in vivo to Leucine[5]-Enkephalin was quantified.

Figure 5:
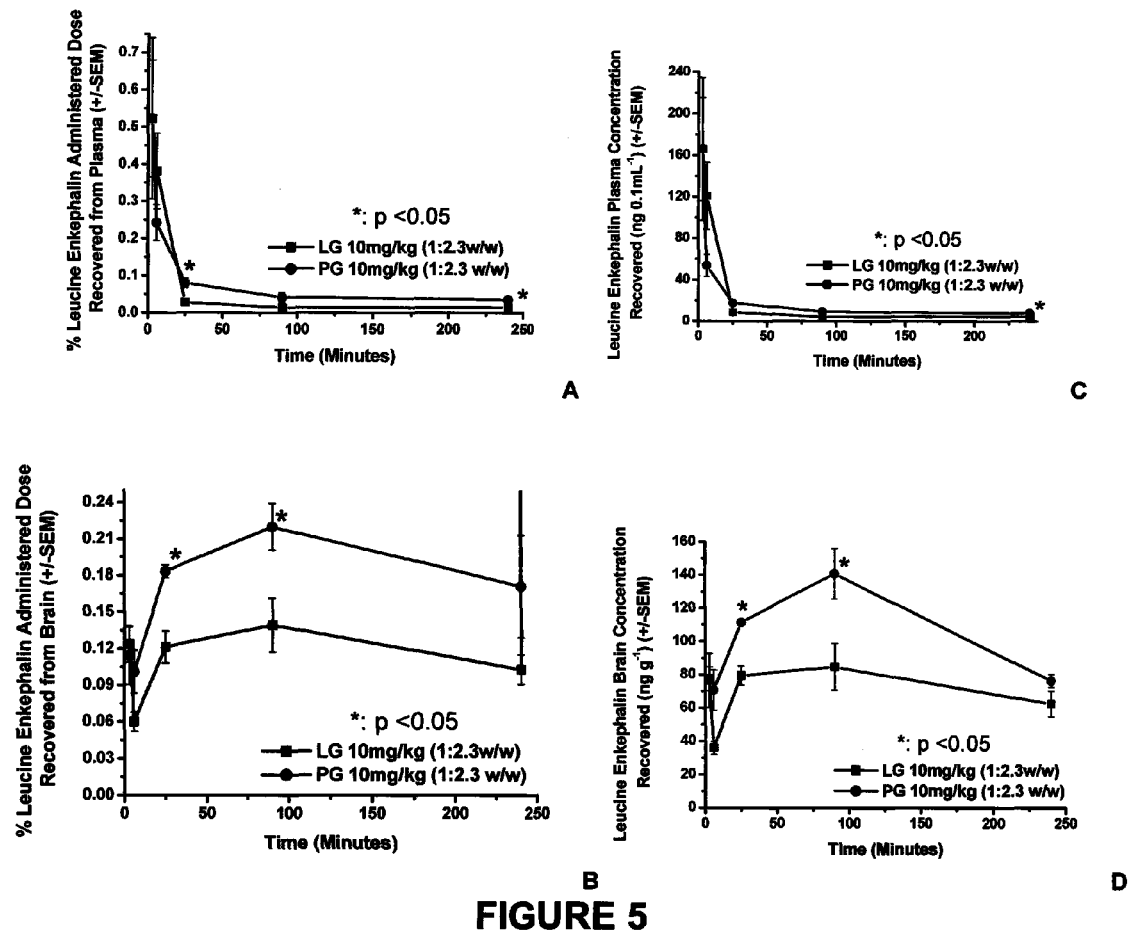
FIG. 5 shows the in vivo concentration of Leucine[5]-Enkephalin following intravenous administration of 10 mg kg$^{-1}$ Leucine[5]-Enkephalin as a nanoparticulate formulation (with GCPQ) and 10 mg kg$^{-1}$ TPLENK (equivalent to 7 mg kg$^{-1}$ of Leucine[5]-Enkephalin) as a nanoparticulate formulation (with GCPQ)
Figure 6:
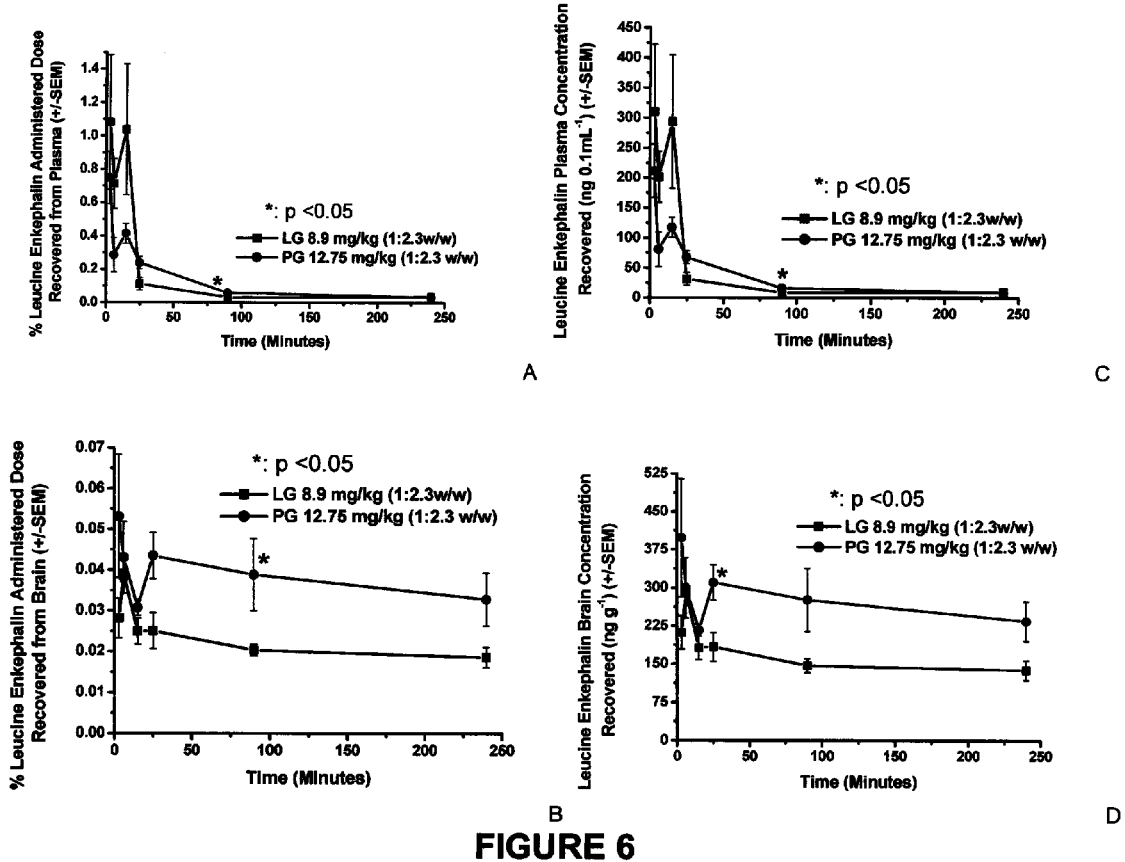
FIG. 6 shows the in vivo concentration of Leucine[5]-Enkephalin following intravenous administration of the equivalent of 8.9 mg kg$^{-1}$ Leucine[5]-Enkephalin either as a nanoparticulate formulation of Leucine[5]-Enkephalin or a nanoparticulate formulation of TPLENK.

On administration of 10 mg kg$^{-1}$ Leucine[5]-Enkephalin and 10 mg kg$^{-1}$ TPLENK (equivalent to 7 mg kg$^{-1}$ of Leucine[5]-Enkephalin) as particulate formulations with GCPQ (FIG. 5), the plasma half-life was increased by 3.2 fold when the nanoparticulate formulation of the lipidic peptide (PG) was used versus the nanoparticulate formulation of Leucine[5]-Enkephalin (LG). The AUC$_{(0-240)}$ in the brain was significantly increased (FIG. 5) when the nanoparticulate formulation of TPLENK was compared to the nanoparticulate formulation of Leucine[5]-Enkephalin. Repeating the IV study of the nanoparticulate formulations of TPLENK and Leucine[5]-Enkephalin with a slightly different dose [8.9 mg kg$^{-1}$ Leucine[5]-Enkephalin and 12.75 mg kg$^{-1}$ TPLENK (equivalent to 8.9 mg kg$^{-1}$ Leucine$^5$-Enkephalin)] also showed a significant increase in AUC$_{(0-240)}$ (FIG. 6). Statistically significantly different plasma and brain levels were achieved for the nanoparticulate formulation of TPLENK when compared to the nanoparticulate formulation of Leucine[5]-Enkephalin at 25 ($p=0.023$) and 240 ($p=0.017$) minutes in plasma and 25 ($p=0.012$) and 90 ($p=0.033$) minutes in brain (FIG. 5). No Leucine[5]-Enkephalin was detected in samples taken from animals receiving Sodium Chloride 0.9% intravenously.

Example 7

Pharmacodynamics—Intravenous Administration

Leucine[5]-Enkephalin causes central analgesic effects in the brain with slight preference for δ-opioid receptors. Occurrence of central analgesic effects would prove the brain targeting of Leucine[5]-Enkephalin-GCPQ particulate formulations and TPLENK-GCPQ particulate formulations in accordance with the preliminary pharmacokinetic data. Leucine[5]-Enkephalin and sodium chloride (0.9% w/v) have been used as controls. Leucine[5]-Enkephalin alone was used in order to observe the equipotent effect of this peptide in the same dose as in the particulate formulations and sodium chloride as a placebo to rule out any effects of endogenously produced neuropeptides during antinociception testing.

Animals

ICR (CD-1) male out bred mice (22-28 g, 4-5 weeks old, Harlan, Oxon, UK) were used. The animals were housed in groups of 5 in plastic cages in controlled laboratory conditions with ambient temperature and humidity maintained at ~22° C. and 60% respectively with a 12-hour light and dark cycle (lights on at 8:00 and off at 20:00). Food and water were available ad libitum and the animals acclimatised for 5-7 days, prior to any experiments, in the Animal House, School of Pharmacy, University of London (London, UK). Animals were only used once and were acclimatised in the testing environment for at least 20 hours prior to testing. All testing was performed in accordance with the recommendations and policies of the Home Office (Animals Scientific Procedures Act 1986, UK) and the Ethics Committee of the School of Pharmacy, University of London guidelines for the care and use of laboratory animals.

Syringes were attached to 26 G×⅝ inches (0.45 mm×16 mm, BD Microlance™ 3) for intravenous administration.

Formulations

This study included four arms: (i) Placebo: Sodium Chloride 0.9%, (ii) Leucine[5]-Enkephalin (L), (iii) Leucine[5]-Enkephalin and GCPQ (LG) and (iv) TPLENK and GCPQ (PG). Animals were administered 14 mg Kg$^{-1}$ Leucine[5]-Enkephalin (L and LG) or 20 mg Kg$^{-1}$ TPLENK (PG). Sodium Chloride 0.9% (pH 7.4) was used as the disperse phase. The final formulation concentration of peptides was 5 or 3 mg mL$^{-1}$ with a ratio of peptide to polymer of 1:2.3 w/w. All formulations were prepared by vortexing (WhirliMixer, Fisherbrand) and then by probe sonication (MSE Soniprep 150) with the instrument set at 50% of its maximum output for 15 minutes on ice. The formulations were left overnight in the fridge. The administered volume was set to a maximum of 0.2 ml per mouse. The administered volume was adjusted based on HPLC quantification of Leucine[5]-Enkephalin and TPLENK and the body weight of each animal. The maximum volume was dosed for placebo (sodium chloride) receiving mice.

Antinociception Studies

Antinociception was assessed in mice using the tail flick warm water bioassay (D'Amour and Smith 1941; Mogil et al. 1999). The protruding distal half of the tail (4-5 cm) of confined mice in a Plexiglas restrainer was immersed in circulating warm water maintained at 55° C.±0.1° C. (Tjolsen and Hole 1993; Polt et al. 1994) by a thermostatically controlled water bath (W14, Grant Instruments, Cambridge Ltd, Herts, UK). Before any experiment was performed the temperature was checked using a thermometer (Gallenkamp, Griffin, THL-333-020L, 76 mm×1 mm, UK). The response latency times, in centiseconds, recorded for each mouse to withdraw its tail by a "sharp flick" were recorded using a digital stopwatch capable of measuring $\frac{1}{100}^{th}$ of a second. The first sign of a rapid tail flick was taken as the behavioural endpoint which followed in most cases 1-3 slow tail movements. Three separate withdrawal latency determinations (separated by ≧20 sec) were averaged (Polt et al. 1994) and individual time points were at least 10 minutes apart. The tails of the mice were wiped dry immediately after testing to prevent the hot water from clinging to the tail producing erythema. Mice not responding within 5 sec were excluded from further testing (Baseline cut-off=5 seconds) and the baseline latency was measured for all mice 2 hours prior testing. Maximum possible cut-off was set to 10 seconds to avoid unnecessary damage to the tail (Tjolsen and Hole 1993). A maximum score was assigned (100%) to animals not responding within 10 seconds to the thermal stimuli. The response times were then converted to percentage of maximum possible effect (% MPE) by a method reported previously (Polt et al. 1994). Briefly, percent antinociception was calculated as 100%× (test latency−baseline latency)/(10 seconds−baseline latency). Data are presented as the mean±SEM for groups of 8 mice per arm. Data are also presented in the quantal form of the tail flick test (number of mice that exhibited maximum latencies to thermal stimuli) which ensures no false positive responses (DAmour and Smith 1941). An analgesic responder was defined as one whose response tail flick latency was two or more times the value of the baseline latency (Shimoyama et al. 1997).

Statistical Analysis

All results were expressed as mean±standard error (i.e. SE: SD/$\sqrt{n}$). A one-way ANOVA test using Minitab 16 was done to assess any statistical difference among the means of % MPE for the different arms of the study. A post-hoc analysis (Tukey's Test) was performed to determine the groups, which show significant difference. In each case, a p-value less than 0.05 was considered as a representation of a significant difference.

Intravenous Peptide Delivery Results

Average baseline latency for intravenously dosed animals was determined to be 1.84±0.62 (Mean±SD) sec. Maximal possible latencies were reached for none, none, four and four mice out of 8 for sodium chloride (0%), L (0%), LG (50%) and PG (50%) respectively. The number of analgesic responders (defined as one whose response was 2 or more times the value of the baseline latency) was none, three, eight and eight out of 8 for sodium chloride (0%), L (37.5%), LG (100%) and PG (100%) respectively. Response time latencies for treated and control animals (FIG. 6) showed statistically significant differences (p<0.05): between PG versus NaCl (25, 45, 60, 90, 120, 150, 180 minutes, p=0.036, <0.0001, 0.005, 0.001, <0.0001, 0.014, 0.007 respectively), PG versus L (45, 90, 120 minutes, p=<0.0001, 0.001, <0.0001 respectively), LG versus NaCl (60, 90, 120, 180 minutes, p=0.005, 0.001, <0.0001, 0.007 respectively), LG versus L (90 minutes, p=0.001) but not between Leucine[5]-Enkephalin (L) versus NaCl or PG versus LG at any of the time points.

Figure 7:
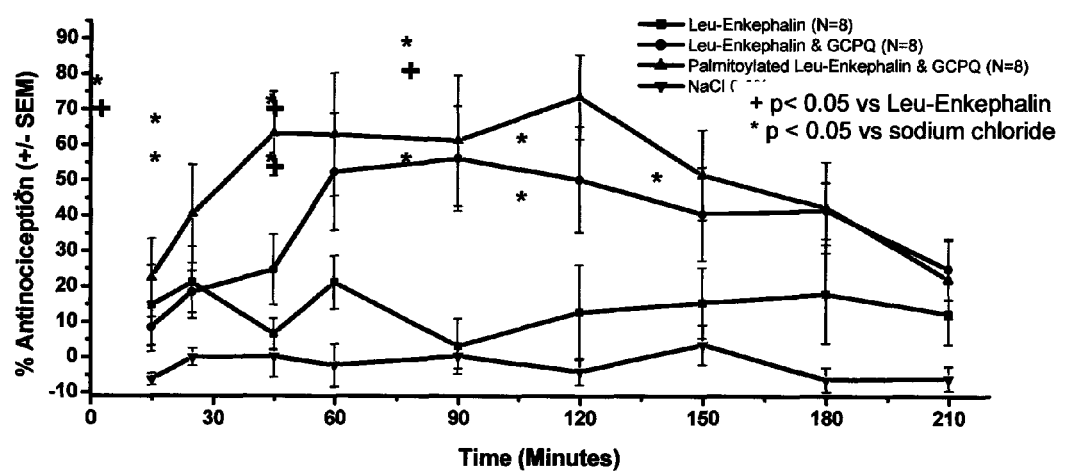
FIG. 7 shows the % antinociception at equivalent does of Leucine[5]-Enkephalin (14 mg kg$^{-1}$) after intravenous administration of Leucine[5]-Enkephalin to CD-1 mice (n=8).

FIG. 7 shows the mean % antinociception (+/−SE) at equivalent doses after IV administration of the peptide formulations to the CD-1 mice (n=8). The ANOVA statistically different groups are: *: p<0.05 vs NaCl, +: p<0.05 vs Leucine[5]-Enkephalin.

A number of patent and non-patent publications are cited in the foregoing specification in order to describe the state of the art to which this invention pertains. The entire disclosure of each of these publications is incorporated by reference herein.

References

Ahmed, M., A. Bjurholm, et al. (1994). "Extraction of neuropeptides from joint tissue for quantification by radioimmunoassay. A study in the rat." Peptides 15(2): 317-22.

Barlos, K., D. Gatos, et al. (1991). "Application of 2-chlorotrityl resin in solid phase synthesis of (Leu15)-gastrin I and unsulfated cholecystokinin octapeptide. Selective O-deprotection of tyrosine." Int J Pept Protein Res 38(6): 555-61.

Beduneau, A., F. Hindre, et al. (2008). "Brain targeting using novel lipid nanovectors." Journal of Controlled Release 126(1): 44-49.

Begley, D. J. (1996). "The blood-brain barrier: Principles for targeting peptides and drugs to the central nervous system." Journal of Pharmacy and Pharmacology 48(2): 136-146.

Begley, D. J. (2004). "ABC transporters and the blood-brain barrier." Current Pharmaceutical Design 10(12): 1295-1312.

Bihorel, S., G. Camenisch, et al. (2007). "Modulation of the brain distribution of imatinib and its metabolites in mice by valspodar, zosuquidar and elacridar." Pharmaceutical Research 24(9): 1720-1728.

D'Amour, F. E. and D. L. Smith (1941). "A method for determining loss of pain sensation." JPET 72: 74-79.

De Ceballos, M. L., M. D. Taylor, et al. (1991). "Isocratic Reverse-Phase HPLC Separation and RIA Used in the Analysis of Neuropeptides in Brain Tissue." Neuropeptides 20: 201-9.

Deeken, J. F. and W. Loscher (2007). "The blood-brain barrier and cancer: Transporters, treatment, and Trojan horses." Clinical Cancer Research 13(6): 1663-1674.

Domard, A., M. Rinaudo, et al. (1986). "New method for the quaternisation of chitosan." Int. J. Biol. Macromol. 8: 105-7.

Girod, J., L. Fenart, et al. (1999). "Transport of cationized anti-tetanus Fab' 2 fragments across an in vitro blood-brain barrier model: Involvement of the transcytosis pathway." Journal of Neurochemistry 73(5): 2002-2008.

Kreuter, J., P. Ramge, et al. (2003). "Direct evidence that polysorbate-80-coated poly(butylcyanoacrylate) nanoparticles deliver drugs to the CNS via specific mechanisms requiring prior binding of drug to the nanoparticles." Pharmaceutical Research 20(3): 409-416.

Lu, W., Q. Sun, et al. (2006). "Cationic albumin-conjugated pegylated nanoparticles allow gene delivery into brain tumors via intravenous administration." Cancer Research 66(24): 11878-11887.

Mogil, J. S., S. G. Wilson, et al. (1999). "Heritability of nociception I: responses of 11 inbred mouse strains on 12 measures of nociception." Pain 80(1-2): 67-82.

Pardridge, W. M. (2005). "The Blood-Brain Barrier: Bottleneck in Brain Drug Development." J. Am. Soc. Exp NeuroTherap. 2: 3-14.

Pardridge, W. M. (2007). "Drug targeting to the brain." Pharmaceutical Research 24(9): 1733-1744.

Polt, R., F. Porreca, et al. (1994). "Glycopeptide enkephalin analogues produce analgesia in mice: evidence for penetration of the blood-brain barrier." Proc Natl Acad Sci USA 91(15): 7114-8.

Qu, X., V. V. Khutoryanskiy, et al. (2006). "Carbohydrate-based micelle clusters which enhance hydrophobic drug bioavailability by up to 1 order of magnitude." Biomacromolecules 7(12): 3452-9.

Qu, X. Z., V. V. Khutoryanskiy, et al. (2006). "Carbohydrate-based micelle clusters which enhance hydrophobic drug bioavailability by up to 1 order of magnitude." Biomacromolecules 7(12): 3452-3459.

Shimoyama, N., M. Shimoyama, et al. (1997). "d-Methadone is antinociceptive in the rat formalin test." J Pharmacol Exp Ther 283(2): 648-52.

Tjolsen, A. and K. Hole (1993). "The tail-flick latency is influenced by skin temperature." AAPS J. 2: 107-111.

Uchegbu, I. F., L. Sadiq, et al. (2001). "Quaternary ammonium palmitoyl glycol chitosan—a new polysoap for drug delivery." Int J Pharm 224(1-2): 185-99.

Wang, W., A. M. McConaghy, et al. (2001). "Controls on polymer molecular weight may be used to control the size of palmitoyl glycol chitosan polymeric vesicles." Langmuir 17(3): 631-636.

Wang, W., A. M. McConaghy, et al. (2001). "Controls on polymer molecular weight may be used to control the size of palmitoyl glycol chitosan polymeric vesicles." Langmuir 17: 631-6.

Wu, Q., K. Hultenby, et al. (2005). "Tissue levels of Leucine [5]-Enkephalin in rats with adjuvant arthritis." J Neuroimmunol 158(1-2): 34-9.

The invention claimed is:

1. A composition comprising a lipophilic derivative of the hydrophilic neuropeptide Leucine[5]-Enkephalin and an amphiphile compound, wherein the derivative comprises a lipophilic linker attached to the side chain oxygen of the tyrosine in the Leucine[5]-Enkephalin, wherein the linker is of the formula —C(C=O)R$^1$, wherein R$^1$ is C$_{4-20}$ alkyl;

wherein the amphiphile compound is quaternary palmitoyl glycol chitosan (GCPQ); and wherein the composition is formulated for human or animal administration by all routes except for the topical route.

2. A composition according to claim 1, wherein the ratio of amphiphile compound to Leucine[5]-Enkephalin derivative in the composition is around 5:1.

3. A pharmaceutical composition comprising a lipophilic derivative of the hydrophilic neuropeptide Leucine[5]-Enkephalin, an amphiphile compound and one or more pharmaceutically acceptable excipients, wherein the derivative comprises a lipophilic linker attached to the side chain oxygen of the tyrosine in the Leucine[5]-Enkephalin, wherein the linker is of the formula —C(C=O)R$^1$, wherein R$^1$ is C$_{4-20}$ alkyl;

wherein the amphiphile compound is quaternary palmitoyl glycol chitosan (GCPQ); and wherein the composition is formulated for human or animal administration by all routes except for the topical route.

4. A method of medical treatment of a condition in a human or animal body, said condition being selected from the group of schizophrenia, obesity, pain and sleep disorders, and psychiatric diseases, said method comprising the administration to a human or animal body in need of said treatment a composition according to claim 1 wherein the composition is not administered via topical route.

5. A method according to claim 4, wherein the composition is orally or intravenously administered to the human or animal body.

6. The composition according to claim 1, wherein the composition is formulated for administration via a route selected from gastrointestinal delivery, parenteral delivery, or mucosal delivery.

7. The method according to claim 4, wherein the composition is administered to the human or animal body via gastrointestinal delivery, parenteral delivery, or mucosal delivery.

* * * * *

UNITED STATES PATENT AND TRADEMARK OFFICE
CERTIFICATE OF CORRECTION

PATENT NO. : 8,278,277 B2
APPLICATION NO. : 12/420896
DATED : October 2, 2012
INVENTOR(S) : Ijeoma Uchegbu, Aikaterini Lalatsa and Andreas Schatzlein It is certified that error appears in the above-identified patent and that said Letters Patent is hereby corrected as shown below:

In the Claims:

Column 23,
Lines 3-4, "formula $-C(C=O)R^1$" should read --formula $-C(=O)R^1$--.
Lines 19-20, "formula $-C(C=O)R^1$" should read --formula $-C(=O)R^1$--.

Signed and Sealed this
Ninth Day of July, 2013

Teresa Stanek Rea
*Acting Director of the United States Patent and Trademark Office*